(12) United States Patent
Maguire et al.

(10) Patent No.: US 11,993,811 B2
(45) Date of Patent: May 28, 2024

(54) SYSTEMS AND METHODS FOR IDENTIFYING AND QUANTIFYING GENE COPY NUMBER VARIATIONS

(71) Applicant: MYRIAD WOMEN'S HEALTH, INC., South San Francisco, CA (US)

(72) Inventors: Jared Robert Maguire, Oakland, CA (US); Alexander D. Robertson, San Francisco, CA (US); Eric Andrew Evans, Brisbane, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 801 days.

(21) Appl. No.: 15/883,944

(22) Filed: Jan. 30, 2018

(65) Prior Publication Data

US 2018/0237845 A1    Aug. 23, 2018

Related U.S. Application Data

(60) Provisional application No. 62/452,985, filed on Jan. 31, 2017.

(51) Int. Cl.
*G16B 20/10* (2019.01)
*C12Q 1/6858* (2018.01)
(Continued)

(52) U.S. Cl.
CPC ......... *C12Q 1/6858* (2013.01); *C12Q 1/6869* (2013.01); *G16B 20/10* (2019.02); *G16B 30/10* (2019.02)

(58) Field of Classification Search
CPC ............................ G16B 20/10; C12Q 2537/16
See application file for complete search history.

(56) References Cited

U.S. PATENT DOCUMENTS

| 7,888,024 B2 | 2/2011 | Hosono |
| 2012/0046877 A1* | 2/2012 | Hyland ................. G16B 20/20 702/20 |

(Continued)

OTHER PUBLICATIONS

Bellos, Evangelos, et al. "cnvCapSeq: detecting copy number variation in long-range targeted resequencing data." Nucleic acids research 42.20 (2014): e158-e158. (Year: 2014).*

(Continued)

*Primary Examiner* — Jesse P Frumkin
(74) *Attorney, Agent, or Firm* — Foley & Lardner LLP

(57) ABSTRACT

A method of identifying and quantifying copy number variations in a gene of interest for a genomic DNA sample includes (i) fragmenting a genomic DNA sample to produce a plurality of polynucleotide fragments, (ii) isolating a plurality of target polynucleotide fragments, (iii) sequencing the plurality of target polynucleotide fragments, (iv) aligning fragment sequences to a reference sequence, (v) calculating read depths for base positions of the plurality of target polynucleotide fragments, (vi) calculating copy number likelihoods for each base position of the reference sequence, (vii) performing a breakpoint analysis on a set of fragment sequences to identify at least one sequence variation located between selected breakpoint regions of the target gene and calculate modified copy number likelihoods for base positions of the reference sequence based on the at least one sequence variation, and (viii) determining whether the target gene includes at least one copy number variation.

20 Claims, 13 Drawing Sheets
Specification includes a Sequence Listing.

(51) Int. Cl.
*C12Q 1/6869* (2018.01)
*G16B 30/10* (2019.01)

(56) References Cited

U.S. PATENT DOCUMENTS

| | | | |
|---|---|---|---|
| 2013/0184999 | A1 | 7/2013 | Ding |
| 2014/0274745 | A1 | 9/2014 | Chen |
| 2014/0342354 | A1 | 11/2014 | Evans |
| 2015/0056619 | A1* | 2/2015 | Li .................. C12Q 1/68 702/19 |
| 2015/0094212 | A1* | 4/2015 | Gottimukkala ...... C12Q 1/6869 702/20 |
| 2015/0203907 | A1* | 7/2015 | Gilbert .................. C12N 15/00 506/2 |
| 2016/0188793 | A1* | 6/2016 | Muzzey ................ G16B 30/10 506/2 |
| 2016/0300013 | A1* | 10/2016 | Ashutosh ............... G16B 20/10 |
| 2020/0032323 | A1* | 1/2020 | Talasaz ................. G16B 30/00 |
| 2022/0101944 | A1* | 3/2022 | Ivanov .................. G16B 30/00 |

OTHER PUBLICATIONS

Altschul et al., "Gapped BLAST and PSI-BLAST: a new generation of protein databaase search programs", Nucleic Acids Research, 1997, vol. 25, No. 17 3389-3402.
Altschul, S.F., et al., "Basic Local Alignment Search Tool", 1990, J. Mol. Biol. 215:403-410.
Boufounos et al., "Basecalling using hidden Markov models", Journal of the Franklin Inst., 341:23-26, 2004.
International Search Report and Written Opinion issued in PCT/US2018/015934 dated Apr. 23, 2018 (10 pages).
Li et al., "The Sequence Alignment/Map format and SAMtools", Bioinformatics, 2009, 25(16):2078-9.
Maccallum et al., "Quantifying copy number variations using a hidden Markov model with inhomogeneous emission distributions", Biostatics, Jul. 1, 2013, 14(3):600-611.
Ning, et al. SSAHA: a fast search method for large DNA databases. Genome Res. Oct. 2001;11(10):1725-9.

\* cited by examiner

SYSTEMS AND METHODS FOR IDENTIFYING AND QUANTIFYING GENE COPY NUMBER VARIATIONS

CROSS-REFERENCE TO RELATED APPLICATIONS

This application claims the benefit of U.S. Provisional Patent Application No. 62/452,985, filed Jan. 31, 2017 and titled SYSTEMS AND METHODS FOR IDENTIFYING AND QUANTIFYING GENE COPY NUMBER VARIATIONS, the disclosure of which is incorporated by reference herein in its entirety.

INCORPORATION OF SEQUENCE LISTING

The instant application contains a Sequence Listing which has been submitted electronically in ASCII format and is hereby incorporated by reference in its entirety. Said ASCII copy, created on May 9, 2018, is named 04268_030_US1 SL.txt and is 783 bytes in size.

BACKGROUND

Research has identified numerous diseases having a genetic basis. Genetic diseases are caused by an abnormality in a person's genome ranging from a discrete mutation in a single genomic deoxyribonucleic acid (DNA) base of a gene to gross chromosome abnormalities. Such genetic abnormalities may result in disease or increased risk of disease, such as in increased risk of cancer, in the individual. In many cases individuals having a genetic abnormality and showing no symptoms may be a carrier for a genetic disease that may be passed to their offspring. Genetic screenings testing for a variety of genetic factors are increasingly available to individuals planning to have children. Genetic screenings may look at a variety of factors that individuals may consider as they are planning for their families.

Certain genetic disorders have been found to be associated with copy-number variations in sections of a person's genome that are repeated. The number of repeats of a particular gene may vary between individuals, with certain copy numbers of the gene in an individual genome being associated with a particular genetic disorder. For example, if an individual has an abnormal copy number of a specified gene in their genome, they may exhibit symptoms of a corresponding genetic disease, have an increased risk of a disease such as cancer, or they may be a carrier of a genetic disease with little or no observable symptoms of the disease. Screening for copy number variations in target genes may assist individuals by alerting them they have a genetic abnormality that may affect them or that they may be at an increased risk for passing a genetic disease to their offspring.

Conventionally, information about genetic alterations have been assayed using conventional procedures for genetic testing, such as fluorescence in situ hybridization (FISH), quantitative fluorescence PCR (QF-PCR) and array-Comparative Genomic Hybridization (array-CGH) and more recently, next generation sequencing (NGS). NGS procedures allow small-scale, inexpensive genome sequencing with a turnaround time measured in days. However, as NGS is generally performed and understood, all regions or loci of the genome are sequenced with roughly equal probability, meaning that a large amount of genomic sequence is collected and discarded to collect sequence information from the relatively low percentage of areas where function is understood well enough to interpret potential mutations.

Generally, purifying samples of regions one is interested in, from a full-genome, is conducted as a separate step from sequencing. It is usually a days-long, low efficiency process in the current state of the art.

There is a need in the art for improved methods and systems for analyzing genomic sequences of regions or loci of interest that may be associated with potentially adverse genetic abnormalities.

SUMMARY

As will be described in greater detail below, the instant disclosure describes various systems and methods for identifying and quantifying copy number variations in a gene of interest for a genomic DNA sample.

In one example, a method for identifying and quantifying copy number variations in a gene of interest for a genomic DNA sample may include (i) fragmenting a genomic DNA sample having an unknown copy number for regions of a target gene to produce a plurality of polynucleotide fragments, (ii) isolating a plurality of target polynucleotide fragments from the plurality of polynucleotide fragments, each of the plurality of target polynucleotide fragments including at least a portion of the target gene, (iii) sequencing the plurality of target polynucleotide fragments to obtain a plurality of fragment sequences, (iv) aligning fragment sequences of the plurality of fragment sequences to a reference sequence, (v) calculating read depths for base positions of the plurality of target polynucleotide fragments relative to each base position of the reference sequence, (vi) calculating copy number likelihoods for each base position of the reference sequence based on the read depths, (vii) performing a breakpoint analysis on a set of fragment sequences of the plurality of fragment sequences to identify at least one sequence variation located between selected breakpoint regions of the target gene and calculate modified copy number likelihoods for base positions of the reference sequence based on the at least one sequence variation, the modified copy number likelihoods each including a modification to a respective copy number likelihood indicating an increase or decrease in evidence for a copy number variation in the target gene at the corresponding base position of the reference sequence, and (viii) determining, based on the modified copy number likelihoods for the base positions of the reference sequence, whether the target gene includes at least one copy number variation.

In at least one embodiment, the method may further include partitioning each of the plurality of fragment sequences to either the target gene or a homolog of the target gene, wherein aligning the fragment sequences of the plurality of fragment sequences to the reference sequence comprises aligning fragment sequences partitioned to the target gene to the reference sequence, which is a target gene reference sequence. The method may further include aligning additional fragment sequences partitioned to the homolog of the target gene to a homolog gene reference sequence.

In some embodiments, the set of fragment sequences on which the breakpoint analysis is performed may include fragment sequences that are at least partially located between the selected breakpoint regions of the target gene. The set of fragment sequences on which the breakpoint analysis is performed may include fragment sequences that include the selected breakpoint regions of the target gene. The fragment sequences that include the selected breakpoint regions of the target gene may include a sequence variation on one side of at least one of the selected breakpoint regions.

In various embodiments, the plurality of target polynucleotide fragments may be isolated with a plurality of probes that hybridize to selected portions of each of the target polynucleotide fragments. The plurality of probes may be hybrid capture probes. The set of fragment sequences on which the breakpoint analysis is performed may include fragment sequences having portions that hybridize to breakpoint probes of the plurality of probes. The breakpoint probes may include probes of the plurality of probes that hybridize to sequence regions located closest to the selected breakpoint regions with respect to the reference sequence. The breakpoint probes may each be designed to target a selected breakpoint region observed in at least one other sample. The breakpoint probes may include probes of the plurality of probes that hybridize to sequence regions located between the selected breakpoint regions with respect to the reference sequence.

In at least one embodiment, performing the breakpoint analysis on the set of fragment sequences of the plurality of fragment sequences may further include determining a likelihood that each of a plurality of types of sequence variation are present between the selected breakpoint regions of the target gene. The plurality of types of sequence variation may respectively correspond to a plurality of types of copy number variation and no copy number variation. The plurality of types of sequence variation may include a deletion, an insertion, an inversion, a translocation, an interchange, and a fusion. The plurality of types of copy number variation may respectively correspond to at least one deletion and at least one duplication of one or more of the regions of the target gene. In some embodiments, determining whether the target gene includes at least one copy number variation may include determining, above a threshold probability, that the at least one sequence variation is present between the selected breakpoint regions of the target gene based on the respective likelihoods calculated for the plurality of types of sequence variation.

In some embodiments, the breakpoint analysis may be performed when the copy number likelihoods calculated based on read depths for base positions located between the selected breakpoint regions are below a specified threshold. The reference sequence may include a sequence from a reference genome. Calculating the modified copy number likelihoods for the base positions of the reference sequence may include calculating normalized read depths for the base positions of the plurality of target polynucleotide fragments relative to each base position of the reference sequence.

A system for identifying and quantifying copy number variations in a gene of interest for a genomic DNA sample may include (i) a next generation sequencing device that fragments a genomic DNA sample having an unknown copy number for regions of a target gene to produce a plurality of polynucleotide fragments, isolates a plurality of target polynucleotide fragments from the plurality of polynucleotide fragments, each of the plurality of target polynucleotide fragments including at least a portion of the target gene, and sequences the plurality of target polynucleotide fragments to obtain a plurality of fragment sequences, (ii) an alignment module, stored in memory, that aligns fragment sequences of the plurality of fragment sequences to a reference sequence, (iii) a read depth module, stored in memory, that calculates read depths for base positions of the plurality of target polynucleotide fragments relative to each base position of the reference sequence and calculates copy number likelihoods for each base position of the reference sequence based on the read depths, (iv) a breakpoint module, stored in memory, that performs a breakpoint analysis on a set of fragment sequences of the plurality of fragment sequences to identify at least one sequence variation located between selected breakpoint regions of the target gene and calculate modified copy number likelihoods for base positions of the reference sequence based on the at least one sequence variation, the modified copy number likelihoods each including a modification to a respective copy number likelihood indicating an increase or decrease in evidence for a copy number variation in the target gene at the corresponding base position of the reference sequence, (v) a copy number module, stored in memory, that determines, based on the modified copy number likelihoods for the base positions of the reference sequence, whether the target gene includes at least one copy number variation, and (vi) at least one physical processor that executes the alignment module, the read depth module, the breakpoint module, and the copy number module.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of example embodiments and are a part of the specification. Together with the following description, these drawings demonstrate and explain various principles of the instant disclosure.

Figure 1:
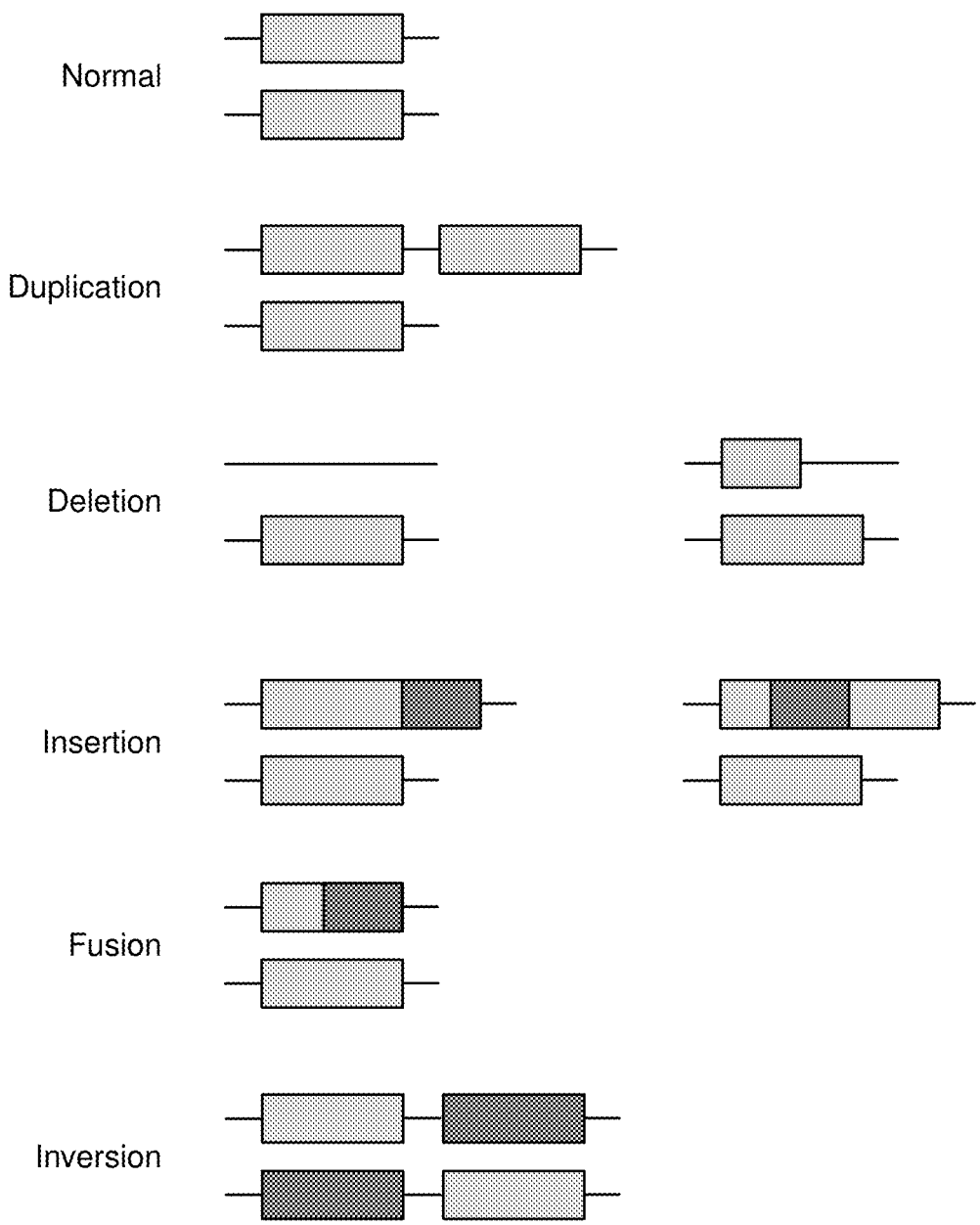
FIG. 1 is a diagram illustrating various types of structural variations in genomic sequences.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the instant disclosure covers all modifications, equivalents, and alternatives falling within the scope of the appended claims.

DETAILED DESCRIPTION OF EXAMPLE EMBODIMENTS

The present disclosure is generally directed to systems and methods for quantitatively determining the copy number of one or more genes of interest in DNA samples. Unless defined otherwise herein, all technical and scientific terms used herein have the same meaning as commonly understood by one of ordinary skill in the art to which this invention belongs. Numeric ranges are inclusive of the numbers defining the range. The term "about" is used herein to mean plus or minus ten percent (10%) of a value. For example, "about 100" refers to any number between 90 and 110. Unless otherwise indicated, nucleic acids are written left to right in 5' to 3' orientation; amino acid sequences are written left to right in amino to carboxy orientation, respectively.

As used herein, "purified" means that a molecule is present in a sample at a concentration of at least 95% by weight, or at least 98% by weight of the sample in which it is contained.

An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromasomally or at a chromosomal location that is different from its natural chromosomal location.

The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program. In the case of a nucleic acid the term also applies to the intronic and/or intergenic regions. For example, as used herein, 80% homology means the same thing as 80% sequence identity determined by a defined algorithm, and accordingly a homolog of a given sequence has greater than 80% sequence identity over a length of the given sequence.

As used herein, "highly homologous" means that the homology between a gene and its corresponding homolog is greater than 90% over a region whose length corresponds to the NGS read length. Thus, a gene and its homolog are referred to as "highly homologous" if any region in the gene is highly homologous to the homolog. An NGS read length may range from 30 nt to 400 nt, from 50 nt to 250 nt, from 50 nt to 150 nt, or from 100 nt to 200 nt. Importantly, the entire gene's sequence need not be "highly homologous" to say a gene has a homolog; only a region in the gene needs to be highly homologous.

The term "homolog" as used herein refers to a DNA sequence that is identical or nearly identical to a gene of interest located elsewhere in the subject's genome. The homolog can be either another gene, a "pseudogene," or a segment of sequence that is not part of a gene. A "pseudogene" as used herein is a DNA sequence that closely resembles a gene in DNA sequence but harbors at least one change that renders it dysfunctional. The change may be a single residue mutation. The change may result in a splice variant. The change may result in early termination of translation. A pseudogene is a dysfunctional relative of a functional gene. Pseudogenes are characterized by a combination of homology to a known gene (i.e., a gene of interest) and nonfunctionality. The number of pseudogenes for genes is not limited to those enumerated herein. Pseudogenes are increasingly recognized. Therefore, a person skilled in the art would be able to determine if a sequence is a pseudogene on the basis of sequence homology or by reference to a curated database such as, for example, GeneCards (genecards.org), pseudogenes.org, etc.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adapters, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component, tag, reactive moiety, or binding partner. Polynucleotide sequences, when provided, are listed in the 5' to 3' direction, unless stated otherwise.

As used herein, a "gene of interest" is a gene for which determining the number of functional copies is desired. Generally, a gene of interest has two functional copies due to the two chromosomes each having a copy of the gene of interest. The terms "gene of interest" and "gene" may be used interchangeably herein.

The term "mutation" as used herein refers to both spontaneous and inherited sequence variations, including, but not limited to, variations between individuals, or between an individual's sequence and a reference sequence. Exemplary mutations include, but are not limited to, SNPs, indel, copy number variants, inversions, translocations, chromosomal fusions, etc. FIG. 1 illustrates exemplary types of mutations that may result in copy number variations or read depth anomalies, and which may be analyzed and/or quantified in accordance with the systems and methods disclosed herein. For example, FIG. 1 illustrates a "normal" pair of homologous gene regions (e.g., exons, genes, etc.) of a diploid chromosome. Also illustrated in FIG. 1 are various types of exemplary copy number variations that may be found in a chromosome region, such as duplication, deletion (full exon deletion and partial exon deletion), insertion, fusion, and inversion. Some examples of chromosomes that have undergone "deletion or duplication" of the gene and/or homolog are shown. Additionally, recombination between a gene and its homolog in a diploid chromosome can yield "fusion" genes that are part "gene" and part "homolog". Further, "interchange" of sequences between gene and homolog is relatively frequent. For many genes with homologs—indeed for the genes that underlie Gaucher's Disease, Spinal Muscular Atrophy ("SMA"), Congenital Adrenal Hyperplasia ("CAH"), and alpha-thalassemia—the gene and homolog are in close proximity to each other on the chromosome.

The term "hybridized" as applied to a polynucleotide refers to a polynucleotide in a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi-stranded complex, a single self hybridizing strand, or any combination of these. The hybridization reaction may constitute a step in a more extensive process, such as the initiation of a PCR reaction, ligation reaction, sequencing reaction, or cleavage reaction.

The practice of the present invention employs, unless otherwise indicated, conventional techniques of immunology, biochemistry, chemistry, molecular biology, microbiology, cell biology, genomics and recombinant DNA, which are within the skill of the art. See e.g. Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Exemplary computer programs which can be used to determine identity between two sequences include, but are not limited to, the suite of BLAST programs, e.g., BLASTN, BLASTX, and TBLASTX, BLASTP and TBLASTN, and BLAT publicly available on the Internet. See also, Altschul, et al., 1990 and Altschul, et al., 1997.

Sequence searches may be carried out, using any suitable software, without limitation, including, for example, using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997).

Alignment of selected sequences in order to determine "% identity" between two or more sequences, may be performed using any suitable software, without limitation, including, for example, the CLUSTAL-W program in MacVector version 13.0.7, operated with default parameters, including an open gap penalty of 10.0, an extended gap penalty of 0.1, and a BLOSUM 30 similarity matrix.

Sequences from a region of interest may be isolated and enriched, where possible, with hybrid-capture probes or PCR primers, which should be designed such that the captured and sequenced fragments contain at least one sequence that distinguishes a gene from its homolog(s). For example, hybrid-capture probes may be designed to anneal adjacent to the few bases that differ between the gene and the homolog(s)/pseudogene(s) ("diff bases"). Where such distinguishing sequence is scarce, multiple probes may be used to capture distinguishable fragments to diminish the effect of biases inherent in each particular probe's sequence. Amplicon sequencing can be used as an alternative to hybrid-capture as a means to achieve targeted sequencing. High-depth whole-genome sequencing can be used as an alternative to targeted sequencing. Any high-throughput quantitative data that reflects the dose of a particular genomic region may be used, be it from NGS, microarrays, or any other high-throughput quantitative molecular biology technique.

In some embodiments, sequences from a region of interest may be isolated with oligonucleotides adhered to a solid support. Oligonucleotides to which the solid support is exposed for attachment may be of any suitable length, and may comprise one or more sequence elements. Examples of sequence elements include, but are not limited to, one or more amplification primer annealing sequences or complements thereof, one or more sequencing primer annealing sequences or complements thereof, one or more common sequences shared among multiple different oligonucleotides or subsets of different oligonucleotides, one or more restriction enzyme recognition sites, one or more target recognition sequences complementary to one or more target polynucleotide sequences, one or more random or near-random sequences (e.g. one or more nucleotides selected at random from a set of two or more different nucleotides at one or more positions, with each of the different nucleotides selected at one or more positions represented in a pool of oligonucleotides comprising the random sequence), one or more spacers, and combinations thereof. Two or more sequence elements can be non-adjacent to one another (e.g. separated by one or more nucleotides), adjacent to one another, partially overlapping, or completely overlapping.

In some embodiments, the oligonucleotide sequence attached to the support or the target sequence to which it specifically hybridizes may comprise a causal genetic variant. In general, causal genetic variants are genetic variants for which there is statistical, biological, and/or functional evidence of association with a disease or trait. A single causal genetic variant can be associated with more than one disease or trait. In some embodiments, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (TRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation).

In some embodiments, a causal genetic variant may be associated with a disease, such as a rare genetic disease. Examples of diseases with which a causal genetic variant may be associated include, but are not limited to: 21-Hydroxylase Deficiency, ABCC8-Related Hyperinsulinism, ARSACS, Achondroplasia, Achromatopsia, Adenosine Monophosphate Deaminase 1, Agenesis of Corpus Callosum with Neuronopathy, Alkaptonuria, Alpha-1-Antitrypsin Deficiency, Alpha-Mannosidosis, Alpha-Sarcoglycanopathy, Alpha-Thalassemia, Alzheimers, Angiotensin II Receptor, Type I, Apolipoprotein E Genotyping, Argininosuccinicaciduria, Aspartylglycosaminuria, Ataxia with Vitamin E Deficiency, Ataxia-Telangiectasia, Autoimmune Polyendocrinopathy Syndrome Type 1, BRCA1 Hereditary Breast/Ovarian Cancer, BRCA2 Hereditary Breast/Ovarian Cancer, one or more other types of cancer, Bardet-Biedl Syndrome, Best Vitelliform Macular Dystrophy, Beta-Sarcoglycanopathy, Beta-Thalassemia, Biotinidase Deficiency, Blau Syndrome, Bloom Syndrome, CFTR-Related Disorders, CLN3-

Related Neuronal Ceroid-Lipofuscinosis, CLN5-Related Neuronal Ceroid-Lipofuscinosis, CLN8-Related Neuronal Ceroid-Lipofuscinosis, Canavan Disease, Carnitine Palmitoyltransferase IA Deficiency, Carnitine Palmitoyltransferase II Deficiency, Cartilage-Hair Hypoplasia, Cerebral Cavernous Malformation, Choroideremia, Cohen Syndrome, Congenital Cataracts, Facial Dysmorphism, and Neuropathy, Congenital Disorder of Glycosylationla, Congenital Disorder of Glycosylation 1b, Congenital Finnish Nephrosis, Crohn Disease, Cystinosis, DFNA 9 (COCH), Diabetes and Hearing Loss, Early-Onset Primary Dystonia (DYTI), Epidermolysis Bullosa Junctional, Herlitz-Pearson Type, FANCC-Related Fanconi Anemia, FGFR1-Related Craniosynostosis, FGFR2-Related Craniosynostosis, FGFR3-Related Craniosynostosis, Factor V Leiden Thrombophilia, Factor V R2 Mutation Thrombophilia, Factor XI Deficiency, Factor XIII Deficiency, Familial Adenomatous Polyposis, Familial Dysautonomia, Familial Hypercholesterolemia Type B, Familial Mediterranean Fever, Free Sialic Acid Storage Disorders, Frontotemporal Dementia with Parkinsonism-17, Fumarase deficiency, GJB2-Related DFNA 3 Nonsyndromic Hearing Loss and Deafness, GJB2-Related DFNB 1 Nonsyndromic Hearing Loss and Deafness, GNE-Related Myopathies, Galactosemia, Gaucher Disease, Glucose-6-Phosphate Dehydrogenase Deficiency, Glutaricacidemia Type 1, Glycogen Storage Disease Type 1a, Glycogen Storage Disease Type 1b, Glycogen Storage Disease Type II, Glycogen Storage Disease Type III, Glycogen Storage Disease Type V, Gracile Syndrome, HFE-Associated Hereditary Hemochromatosis, Halder AIMs, Hemoglobin S Beta-Thalassemia, Hereditary Fructose Intolerance, Hereditary Pancreatitis, Hereditary Thymine-Uraciluria, Hexosaminidase A Deficiency, Hidrotic Ectodermal Dysplasia 2, Homocystinuria Caused by Cystathionine Beta-Synthase Deficiency, Hyperkalemic Periodic Paralysis Type 1, Hyperornithinemia-Hyperammonemia-Homocitrullinuria Syndrome, Hyperoxaluria, Primary, Type 1, Hyperoxaluria, Primary, Type 2, Hypochondroplasia, Hypokalemic Periodic Paralysis Type 1, Hypokalemic Periodic Paralysis Type 2, Hypophosphatasia, Infantile Myopathy and Lactic Acidosis (Fatal and Non-Fatal Forms), Isovaleric Acidemias, Krabbe Disease, LGMD2I, Leber Hereditary Optic Neuropathy, Leigh Syndrome, French-Canadian Type, Long Chain 3-Hydroxyacyl-CoA Dehydrogenase Deficiency, MELAS, MERRF, MTHFR Deficiency, MTHFR Thermolabile Variant, MTRNR1-Related Hearing Loss and Deafness, MTTS1-Related Hearing Loss and Deafness, MYH-Associated Polyposis, Maple Syrup Urine Disease Type 1A, Maple Syrup Urine Disease Type 1B, McCune-Albright Syndrome, Medium Chain Acyl-Coenzyme A Dehydrogenase Deficiency, Megalencephalic Leukoencephalopathy with Subcortical Cysts, Metachromatic Leukodystrophy, Mitochondrial Cardiomyopathy, Mitochondrial DNA-Associated Leigh Syndrome and NARP, Mucolipidosis IV, Mucopolysaccharidosis Type I, Mucopolysaccharidosis Type IIIA, Mucopolysaccharidosis Type VII, Multiple Endocrine Neoplasia Type 2, Muscle-Eye-Brain Disease, Nemaline Myopathy, Neurological phenotype, Niemann-Pick Disease Due to Sphingomyelinase Deficiency, Niemann-Pick Disease Type C1, Nijmegen Breakage Syndrome, PPT1-Related Neuronal Ceroid-Lipofuscinosis, PROP1-related pituitary hormome deficiency, Pallister-Hall Syndrome, Paramyotonia Congenita, Pendred Syndrome, Peroxisomal Bifunctional Enzyme Deficiency, Pervasive Developmental Disorders, Phenylalanine Hydroxylase Deficiency, Plasminogen Activator Inhibitor I, Polycystic Kidney Disease, Autosomal Recessive, Prothrombin G20210A Thrombophilia, Pseudovitamin D Deficiency Rickets, Pycnodysostosis, Retinitis Pigmentosa, Autosomal Recessive, Bothnia Type, Rett Syndrome, Rhizomelic Chondrodysplasia Punctata Type 1, Short Chain Acyl-CoA Dehydrogenase Deficiency, Shwachman-Diamond Syndrome, Sjogren-Larsson Syndrome, Smith-Lemli-Opitz Syndrome, Spastic Paraplegia 13, Sulfate Transporter-Related Osteochondrodysplasia, TFR2-Related Hereditary Hemochromatosis, TPP1-Related Neuronal Ceroid-Lipofuscinosis, Thanatophoric Dysplasia, Transthyretin Amyloidosis, Trifunctional Protein Deficiency, Tyrosine Hydroxylase-Deficient DRD, Tyrosinemia Type I, Wilson Disease, X-Linked Juvenile Retinoschisis, and Zellweger Syndrome Spectrum.

In some embodiments, the oligonucleotide sequence attached to the solid support or the target sequence to which it specifically hybridizes may include an ancestry informative marker (AIM). In general, an AIM is a genetic variant that differs in frequency between two or more populations of individuals, such as two or more human populations, and may be used to infer the ancestry of a subject, either alone or in combination with one or more other AIMs. An AIM may be used to classify a person as belonging to or not belonging to one or more populations, such as a population that is at increased risk for one of the causal genetic variants. For example, an AIM can be diagnostic for a population in which a trait is at increased prevalence.

In some embodiments, a plurality of target polynucleotides may be amplified according to a method that comprises exposing a sample comprising a plurality of target polynucleotides to an apparatus of the invention. In some embodiments, the amplification process comprises bridge amplification. In some embodiments, a plurality of polynucleotides are sequenced according to a method that comprises exposing a sample comprising a plurality of target polynucleotides to an apparatus of the invention.

In some embodiments, target polynucleotides are fragmented into a population of fragmented polynucleotides of one or more specific size range(s). In some embodiments, the amount of sample polynucleotides subjected to fragmentation is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 or more. In some embodiments, fragments are generated from about, less than about, or more than about 1, 10, 100, 1000, 10000, 100000, 300000, 500000, or more genome-equivalents of starting DNA. Fragmentation may be accomplished by methods known in the art, including chemical, enzymatic, and mechanical fragmentation. In some embodiments, the fragmentation is accomplished mechanically by subjecting sample polynucleotides to acoustic sonication. In some embodiments, the fragmentation comprises treating the sample polynucleotides with one or more enzymes under conditions suitable for the one or more enzymes to generate double-stranded nucleic acid breaks. In some embodiments, fragmentation comprises treating the sample polynucleotides with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. In some embodiments, the method includes the step of size selecting the fragments via standard methods such as column purification or isolation from an agarose gel. In some embodiments, the method comprises determining the average and/or median fragment length after fragmentation. In some embodiments, samples having an average and/or median fragment length above a desired threshold are again subjected to fragmentation. In some embodiments, samples having an average and/or median fragment length below a desired threshold are discarded.

In some embodiments, fragmentation may be followed by ligation of adapter oligonucleotides to the fragmented polynucleotides. An adapter oligonucleotide includes any oligonucleotide having a sequence, at least a portion of which is known, that can be joined to a target polynucleotide. Adapter oligonucleotides may contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as an apparatus as described herein, or flow cells as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. In some embodiments, the adapter oligonucleotides joined to fragmented polynucleotides from one sample comprise one or more sequences common to all adapter oligonucleotides and a barcode that is unique to the adapters joined to polynucleotides of that particular sample, such that the barcode sequence can be used to distinguish polynucleotides originating from one sample or adapter joining reaction from polynucleotides originating from another sample or adapter joining reaction. In some embodiments, an adapter oligonucleotide comprises a 5' overhang, a 3' overhang, or both that is complementary to one or more target polynucleotide overhangs. The terms "joining" and "ligation" as used herein, with respect to two polynucleotides, such as an adapter oligonucleotide and a sample polynucleotide, refers to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods.

In some embodiments, adapted polynucleotides are subjected to an amplification reaction that amplifies target polynucleotides in the sample. Amplification primers may be of any suitable length, such as about, less than about, or more than about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, less than about, or more than about 5, 10, 15, 20, 25, 30, 35, 40, 45, 50, or more nucleotides). "Amplification" refers to any process by which the copy number of a target sequence is increased. Methods for primer-directed amplification of target polynucleotides are known in the art, and include without limitation, methods based on the polymerase chain reaction (PCR). Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles.

In some embodiments, the amplification primer may include a barcode. As used herein, the term "barcode" refers to a known nucleic acid sequence that allows some feature of a polynucleotide with which the barcode is associated to be identified. In general, a barcode comprises a nucleic acid sequence that when joined to a target polynucleotide serves as an identifier of the sample from which the target polynucleotide was derived.

Typically, annealing of a primer to its template takes place at a temperature of 25 to 90° C. A temperature in this range will also typically be used during primer extension, and may be the same as or different from the temperature used during annealing and/or denaturation. Once sufficient time has elapsed to allow annealing and also to allow a desired degree of primer extension to occur, the temperature can be increased, if desired, to allow strand separation. At this stage the temperature will typically be increased to a temperature of 60 to 100° C. High temperatures can also be used to reduce non-specific priming problems prior to annealing, and/or to control the timing of amplification initiation, e.g. in order to synchronize amplification initiation for a number of samples. Alternatively, the strands maybe separated by treatment with a solution of low salt and high pH (>12) or by using a chaotropic salt (e.g. guanidinium hydrochloride) or by an organic solvent (e.g. formamide).

Following strand separation (e.g. by heating), a washing step may be performed. The washing step may be omitted between initial rounds of annealing, primer extension and strand separation, such as if it is desired to maintain the same templates in the vicinity of immobilized primers. This allows templates to be used several times to initiate colony formation. The size of colonies produced by amplification on the solid support can be controlled, e.g. by controlling the number of cycles of annealing, primer extension and strand separation that occur. Other factors which affect the size of colonies can also be controlled. These include the number and arrangement on a surface of immobilized primers, the conformation of a support onto which the primers are immobilized, the length and stiffness of template and/or primer molecules, temperature, and the ionic strength and viscosity of a fluid in which the above-mentioned cycles can be performed.

In some embodiments, bridge amplification may be followed by sequencing a plurality of oligonucleotides attached to the solid support. In some embodiments, sequencing comprises or consists of single-end sequencing. In some embodiments, sequencing comprises or consists of paired-end sequencing. Sequencing can be carried out using any suitable sequencing technique, wherein nucleotides are added successively to a free 3' hydroxyl group, resulting in synthesis of a polynucleotide chain in the 5' to 3' direction.

The identity of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the invention, as are techniques using detection of pyrophosphate release (pyrosequencing). Such pyrosequencing based techniques are particularly applicable to sequencing arrays of beads where the beads have been amplified in an emulsion such that a single template from the library molecule is amplified on each bead. In some embodiments, sequencing comprises treating bridge amplification products to remove substantially all or remove or displace at least a portion of one of the immobilized strands in the "bridge" structure in order to generate a template that is at least partially single-stranded. The portion of the template which is single-stranded will thus be available for hybridization with a sequencing primer. The process of removing all or a portion of one immobilized strand in a bridged double-stranded nucleic acid structure may be referred to herein as "linearization."

In some embodiments, a sequencing primer may include a sequence complementary to one or more sequences derived from an adapter oligonucleotide, an amplification primer, an oligonucleotide attached to the solid support, or a combination of these. In general, extension of a sequencing primer produces a sequencing extension product. The number of nucleotides added to the sequencing extension product that are identified in the sequencing process may depend on a number of factors, including template sequence, reaction conditions, reagents used, and other factors. In some embodiments, a sequencing primer is extended along the full length of the template primer extension product from the amplification reaction, which in some embodiments includes extension beyond a last identified nucleotide. In some embodiments, the sequencing extension product is subjected to denaturing conditions in order to remove the sequencing extension product from the attached template strand to which it is hybridized, in order to make the template partially or completely single-stranded and available for hybridization with a second sequencing primer.

In some embodiments, one or more, or all, of the steps of the method described herein may be automated, such as by use of one or more automated devices. In general, automated devices are devices that are able to operate without human direction—an automated system can perform a function during a period of time after a human has finished taking any action to promote the function, e.g. by entering instructions into a computer, after which the automated device performs one or more steps without further human operation. Software and programs, including code that implements embodiments of the present invention, may be stored on some type of data storage media, such as a CD-ROM, DVD-ROM, tape, flash drive, or diskette, or other appropriate computer readable medium. Various embodiments of the present invention can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present invention are described in terms of a general purpose computer, it should be appreciated that the use of a general purpose computer is exemplary only, as other configurations may be used.

In some embodiments, automation may comprise the use of one or more liquid handlers and associated software. Several commercially available liquid handling systems can be utilized to run the automation of these processes (see for example liquid handlers from Perkin-Elmer, Beckman Coulter, Caliper Life Sciences, Tecan, Eppendorf, Apricot Design, Velocity 11 as examples). In some embodiments, automated steps include one or more of fragmentation, end-repair, A-tailing (addition of adenine overhang), adapter joining, PCR amplification, sample quantification (e.g. amount and/or purity of DNA), and sequencing. In some embodiments, hybridization of amplified polynucleotides to oligonucleotides attached to a solid surface, extension along the amplified polynucleotides as templates, and/or bridge amplification is automated (e.g. by use of an Illumina cBot). In some embodiments, sequencing may automated. A variety of automated sequencing machines are commercially available, and include sequencers manufactured by Life Technologies (SOLiD platform, and pH-based detection), Roche (454 platform), Illumina (e.g. flow cell based systems, such as Genome Analyzer, HiSeq, or MiSeq systems). Transfer between 2, 3, 4, 5, or more automated devices (e.g. between one or more of a liquid handler, a bridge amplification device, and a sequencing device) may be manual or automated.

In some embodiments, exponentially amplified target polynucleotides may be sequenced. Sequencing may be performed according to any method of sequencing known in the art, including sequencing processes described herein, such as with reference to other aspects of the invention. Sequence analysis using template dependent synthesis can include a number of different processes. For example, in the ubiquitously practiced four-color Sanger sequencing methods, a population of template molecules is used to create a population of complementary fragment sequences. Primer extension is carried out in the presence of the four naturally occurring nucleotides, and with a sub-population of dye labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the sequence beyond the primer, and are labeled in a manner that permits identification of the terminating nucleotide. The nested fragment population is then subjected to size based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template. Other examples of template dependent sequencing methods include sequence by synthesis processes, where individual nucleotides are identified iteratively, as they are added to the growing primer extension product (e.g., pyrosequencing).

In some embodiments, genetic variation detected by any of the described systems and methods may be used to calculate a plurality of probabilities. Each probability may be a probability of a subject or a subject's present or future offspring having or developing a disease or trait. In general, calculation of a probability that the tested subject has or will develop a disease or trait is based on a level of risk associated with one or more tested causal genetic variants, non-subject sequences, and/or AIMs. For example, if two causal genetic variants contribute to the risk of developing a disease in an additive fashion, then the presence of both causal genetic variants in a subject would indicate that the risk of that disease in the subject is increased by the value resulting from adding the risks associated with each. In general, calculation of a probability that an offspring of the subject will have a disease or trait is based on a level of risk associated with one or more tested causal genetic variants and/or AIMs, and the probability that an offspring will inherit the causal genetic variants and/or AIMs. Risk calculations may be based on risk correlations maintained in one or more databases, which databases may be updated based on external reports and/or records of genotyping results and associated phenotypes of tested subjects. In some embodiments, the calculations are performed by a computer in accordance with instructions contained in a computer readable medium. In some embodiments, the statistical confidence of a probability that the subject or subject's offspring will have or develop a disease or trait is at least about 70%, 80%, 85%, 90%, 95%, 97.5%, 99%, or higher. Confidence may be based on a number of factors, such as confidence in sequencing accuracy, number of associated genetic variants tested, and confidence in the risk associated with each genetic variant.

Figure 2:
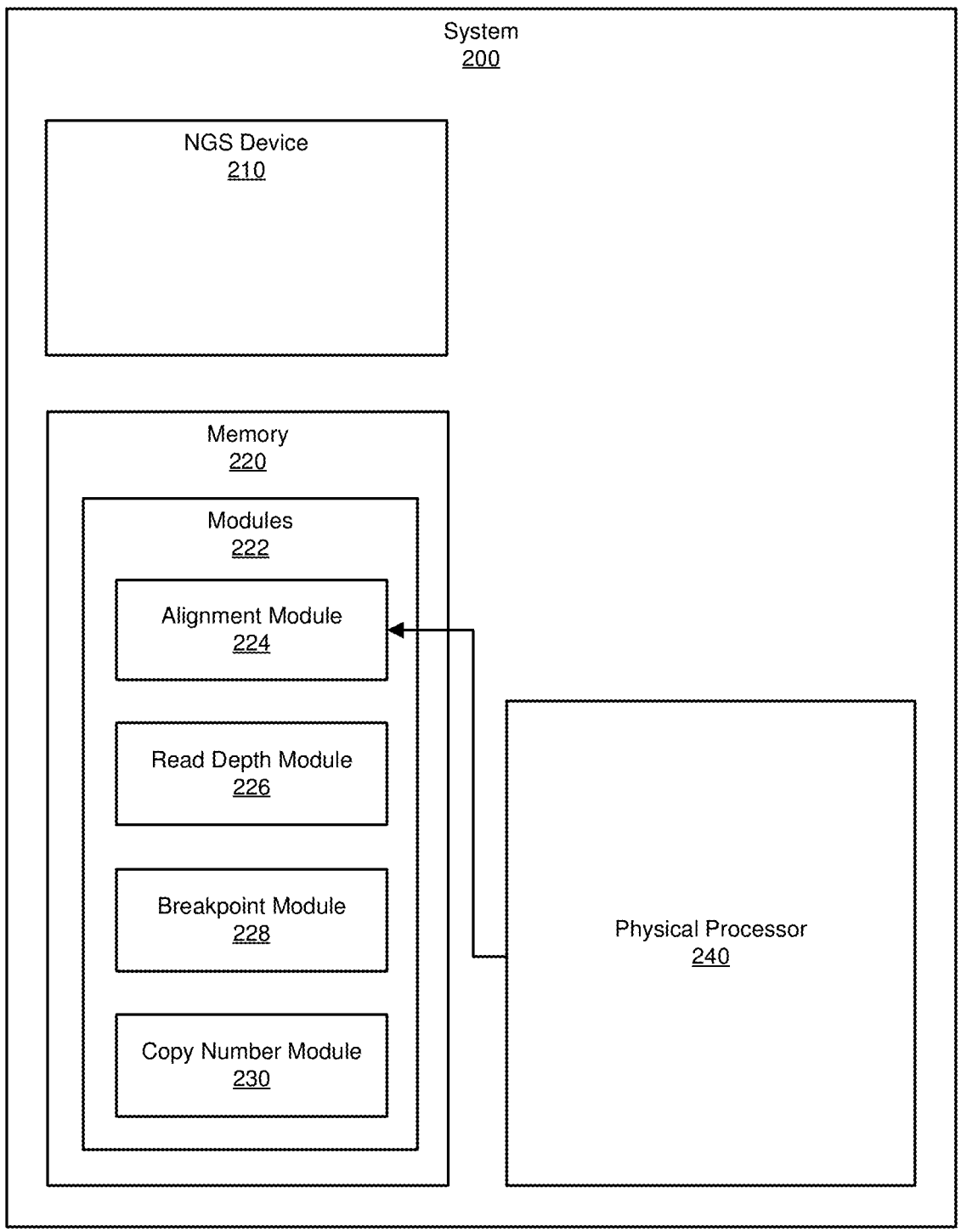
FIG. 2 is a block diagram of an example system for identifying and quantifying copy number variations.

The following will provide, with reference to FIG. 2, detailed descriptions of example systems for identifying and quantifying gene copy number variations. Detailed descriptions of corresponding methods will also be provided in connection with FIG. 3. In addition, detailed descriptions of an example computing system capable of implementing at least a portion of one or more of the embodiments described herein will be provided in connection with FIG. 5.

FIG. 2 is a block diagram of an example system 200 for identifying and quantifying gene copy number variations. As illustrated in this figure, example system 200 may include an NGS device 210 and one or more modules 222 for performing one or more tasks.

NGS device 210 may include any suitable device or a plurality of devices for fragmenting genomic DNA samples, isolating polynucleotide fragments from the DNA samples, and sequencing the isolated polynucleotide sequences. NGS device 210 may include a manual, automated, or semi-automated device for performing any of the NGS procedures and steps as described herein. As will be described in greater detail below, modules 222 may include an alignment module 224 that aligns sequenced polynucleotide sequences, a read depth module 226 that calculates read depths for base positions of the sequenced polynucleotide sequences, a breakpoint module 228 that performs a breakpoint analysis on a set of fragment sequences to calculate modified copy number likelihoods for specified base positions, and a copy number module 230 that determines whether a target gene includes a number variation based on the modified copy number likelihoods.

In certain embodiments, one or more of modules 222 in FIG. 2 may represent one or more software applications or programs that, when executed by a computing device, may cause the computing device to perform one or more tasks. For example, and as will be described in greater detail below, one or more of modules 222 may represent modules stored and configured to run on one or more computing devices. One or more of modules 222 in FIG. 2 may also represent all or portions of one or more special-purpose computers configured to perform one or more tasks. NGS device 210 may also include one or more software applications or programs that, when executed by a computing device, may cause the computing device to perform one or more tasks.

As illustrated in FIG. 2, example system 200 may also include one or more memory devices, such as memory 220. Memory 220 generally represents any type or form of volatile or non-volatile storage device or medium capable of storing data and/or computer-readable instructions. In one example, memory 220 may store, load, and/or maintain one or more of modules 222 and/or one or more modules of NGS device 210. Examples of memory 220 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

As illustrated in FIG. 2, example system 200 may also include one or more physical processors, such as physical processor 240. Physical processor 240 generally represents any type or form of hardware-implemented processing unit capable of interpreting and/or executing computer-readable instructions. In one example, physical processor 240 may access and/or modify one or more of modules 222 stored in memory 220. Additionally or alternatively, physical processor 240 may execute one or more of modules 222 to facilitate identifying message payload bit fields in electronic communications. Examples of physical processor 240 include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, and/or any other suitable physical processor.

Figure 3:
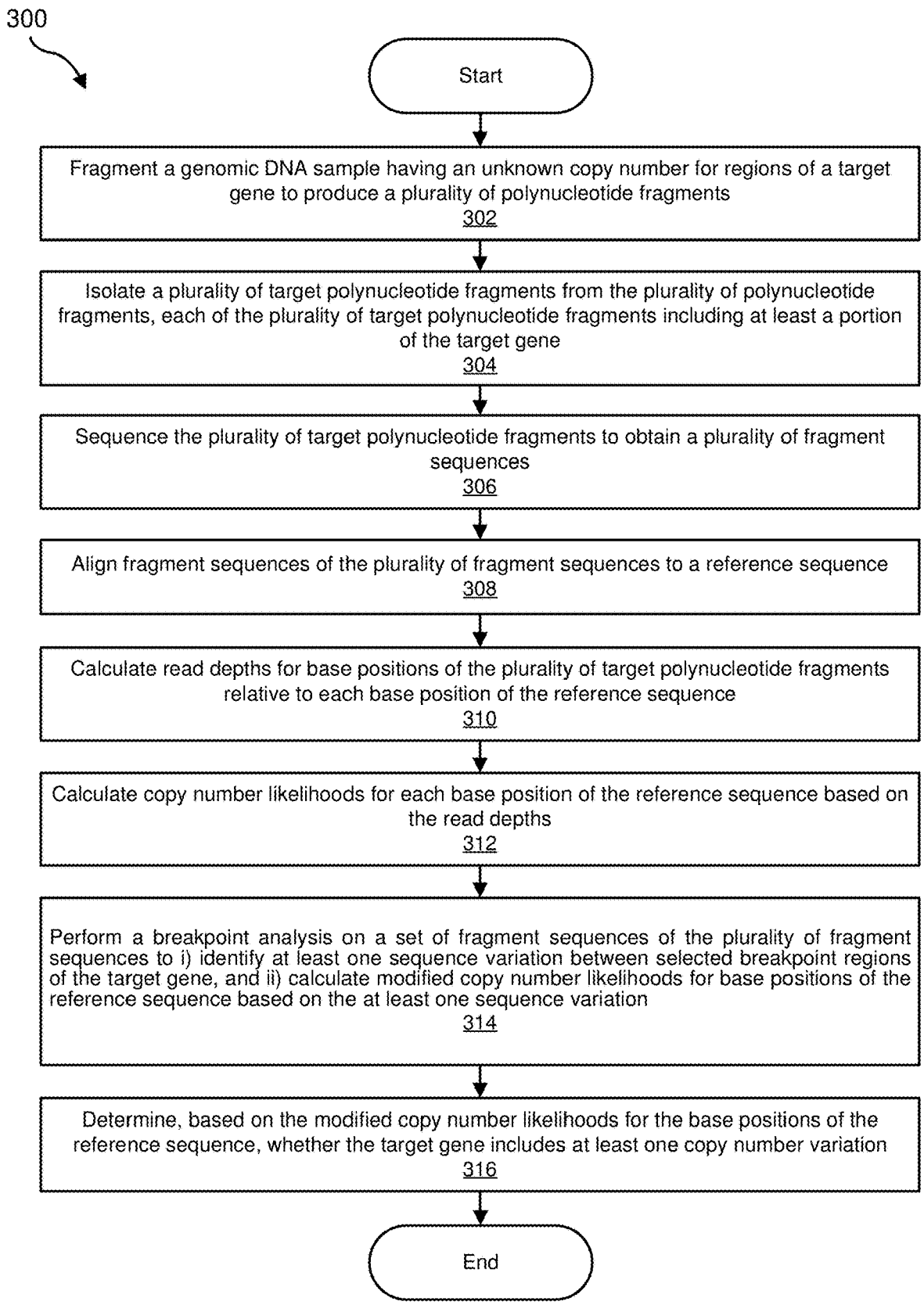
FIG. 3 is a flow diagram of an example method for identifying and quantifying copy number variations.

FIG. 3 is a flow diagram of an exemplary method 300 for identifying and quantifying copy number variations in a gene of interest for a genomic DNA sample. Some of the steps shown in FIG. 3 may be performed by any suitable computer-executable code and/or computing system, including system 200 in FIG. 2. In one example, some of the steps shown in FIG. 3 may represent an algorithm whose structure includes and/or is represented by multiple sub-steps, examples of which will be provided in greater detail below.

As illustrated in FIG. 3, at step 302, one or more of the systems described herein may fragment a genomic DNA sample having an unknown target gene copy number for a target gene to produce a plurality of polynucleotide fragments, the genomic DNA sample including a break point sequence in the target gene. For example, NGS device 210 shown in FIG. 2 may fragment a genomic DNA sample using any of the techniques described herein.

At step 304, one or more of the systems described herein may isolate a plurality of target polynucleotide fragments from the plurality of polynucleotide fragments, each of the plurality of target polynucleotide fragments including at least a portion of the target gene. For example, NGS device 210 shown in FIG. 2 may isolate a plurality of target polynucleotide fragments from the plurality of polynucleotide fragments, each of the plurality of target polynucleotide fragments including at least a portion of the target gene using any of the techniques described herein. In one embodiment, target polynucleotide fragments may be isolated and enriched using probes, such as hybrid-capture probes, directed to specified polynucleotide sequences.

In some embodiments, hybrid-capture probes may be designed to anneal adjacent to the few bases that differ between the gene and the homolog(s)/pseudogene(s) ("diff bases"). Where such distinguishing sequence is scarce, multiple probes may be used to capture distinguishable fragments to diminish the effect of biases inherent to each particular probe's sequence. Amplicon sequencing can be used as an alternative to hybrid-capture as a means to achieve targeted sequencing. High-depth whole-genome sequencing can be used as an alternative to targeted sequencing. Any high-throughput quantitative data that reflects the dose of a particular genomic region may be used, be it from NGS, microarrays, or any other high-throughput quantitative molecular biology technique.

At step 306, one or more of the systems described herein may sequence the plurality of target polynucleotide fragments to obtain a plurality of fragment sequences. For example, NGS device 210 in FIG. 2 may sequence the plurality of target polynucleotide fragments to obtain a plurality of fragment sequences using any of the techniques described herein. In at least one embodiment, the sequenced fragments may contain at least one sequence, including one or more exons of interest, within the target gene.

In some embodiments, each of the plurality of fragment sequences may be partitioned to either the target gene or a homolog of the target gene. Partition reads to a target gene or its homolog(s) based on the presence of the base(s) that distinguish them. The distinguishing base(s) exploited in this partitioning process depend on the particular gene of interest. Further, the partitioning may only use a subset of the distinguishing bases in a given read, again based on the specific application. In an embodiment where a hybrid-capture probe sequence itself becomes part of the sequenced fragment, the hybrid-capture probe may be designed such that the distinguishing base is at or near the terminus of one the ends of a paired-end read. For example in such a case, the hybrid-capture probe may be, e.g., 39 bases long, but the sequencer reads 40 bases from the captured fragment. The probe may be designed such that the 40th base is a distinguishing base, thereby allowing the entire read (i.e., both ends of the paired-end read) to be partitioned to gene or homolog(s) based on the 40th position's base. The precise numbers (i.e., 39 and 40) in the example above could change and yield similar results. In principle, the probe could be as short as 10 bp or as long as 1000 bp, though lengths in the range of 20 bp-100 bp are most common. In embodiments like the one above where the probe becomes part of the sequenced fragment, the sequencer must read beyond the length of the probe by at least 1 bp; however, in embodiments where the captured fragment alone contains enough distinguishing bases to partition the read appropriately to gene or homolog, then sequencing need not necessarily extend beyond the length of the probe.

At step 308, one or more of the systems described herein may align fragment sequences of the plurality of fragment sequences to a reference sequence. For example, alignment module 224 in FIG. 2 may align fragment sequences of the plurality of fragment sequences to a reference sequence.

Alignment may generally involve placing one sequence along another sequence, iteratively introducing gaps along each sequence, scoring how well the two sequences match, and preferably repeating for various positions along the reference. The best-scoring match is deemed to be the alignment and represents an inference about the degree of relationship between the sequences. In some embodiments, a reference sequence to which sequencing reads are compared is a reference genome, such as the genome of a member of the same species as the subject. A reference genome may be complete or incomplete. In some embodiments, a reference genome consists only of regions containing target polynucleotides, such as polynucleotides within and near target genes. In some embodiments, fragment sequences may be aligned to the reference sequence by aligning fragment sequences partitioned to the target gene to the reference sequence, which is a target gene reference sequence. Additional fragment sequences partitioned to the homolog(s) of the target gene may be aligned to homolog gene reference sequence(s).

In an alignment, a base in the sequencing read alongside a non-matching base in the reference may indicate that, for example, a substitution mutation has occurred at that point. Similarly, where one sequence includes a gap alongside a base in the other sequence, an insertion or deletion mutation (an "indel") may be inferred to have occurred. When it is desired to specify that one sequence is being aligned to one other, the alignment is sometimes called a pairwise alignment. Multiple sequence alignment generally refers to the alignment of two or more sequences, including, for example, by a series of pairwise alignments. In some embodiments, scoring an alignment involves setting values for the probabilities of substitutions and indels. When individual bases are aligned, a match or mismatch contributes to the alignment score by a substitution probability, which could be, for example, 1 for a match and 0.33 for a mismatch. An indel deducts from an alignment score by a gap penalty, which could be, for example, −1. Gap penalties and substitution probabilities can be based on empirical knowledge or a priori assumptions about how sequences mutate. Their values may affect the resulting alignment.

The alignment data output may be provided in the format of a computer file. In certain embodiments, the output is a FASTA file, VCF file, text file, or an XML file containing sequence data such as a sequence of the nucleic acid aligned to a sequence of the reference genome. In other embodiments, the output contains coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10): 1725-9 (2001)). In some embodiments, the output is a sequence alignment—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string. In some embodiments, a second alignment using a second algorithm may be performed after a first alignment using a first algorithm. In some examples, filtering based on mapping quality may be optionally performed.

At step 310, one or more of the systems described herein may calculate read depths for base positions of the plurality of target polynucleotide fragments relative to each base position of the reference sequence. For example, read depth module 226 in FIG. 2 may calculate read depths (i.e., depth signal) for base positions of the plurality of target polynucleotide fragments relative to each base position of the reference sequence. Single-end or paired-end reading may be used to determine read depths. The depth of coverage is a measure of the number of times that a specific genomic site is sequenced during a sequencing run. In some embodiments, read depths may be determined and/or normalized based on GC content at each base position of the reference sequence and may be expressed as the number of counts at each base position.

In some embodiments, the abundance of NGS sequence reads bearing gene- or homolog-derived bases may permit distinction between normal (copy number=2) and mutant individuals (copy number 2). Additional useful information is attainable, however, even from sequence reads that cannot distinguish gene from homolog, as in the case of HBA1 and HBA2, where the normal combined copy number of the two identical genes is 4, and a deletion in either gene leads to collective copy number≤3. Note that, in principle, the copy number analysis described herein could be applied even to high-depth whole-genome shotgun sequencing (i.e., without the use of probes for enrichment).

At step 312, one or more of the systems described herein may calculate copy number likelihoods for each base position of the reference sequence based on the read depths. For example, read depth module 226 in FIG. 2 may calculate copy number likelihoods for each base position of the reference sequence based on the read depths. Calculated copy number likelihoods may reflect the general hypothesis that additional copy number duplication in a probed sequence region of a sample results in additional sequence reads in the probed region above expected normal and that copy number deletion results in reduced sequence reads in the probed region below expected normal. A normal copy number in a probed region may be determined based on analysis of sequence reads of reference samples.

Read depth module may include a copy caller that uses any suitable statistical method to calculate the copy number likelihoods. The copy caller may, for example, utilize a statistical model, such as a hidden Markov model (HMM) (Boufounos, P., et al., Journ. of the Franklin Inst. 341: 23-36 (2004)), a Gaussian mixture model, and/or brute force modeling to determine the copy number likelihoods for the base positions. However, these callers have limitations and may produce results that are below a threshold level of probability for certain sequence regions in the target gene. Additionally, such callers may produce calls that are indeterminate and/or that are between two copy numbers, such as a copy number between 1 and 2 (e.g., 1.6 copies, etc.). In some instances, copy callers may produce false positives due to sequence anomalies and/or signal noise at certain sequence regions. A breakpoint caller, as described herein, may be used in conjunctions with a conventional copy caller (e.g., an HMM caller, Gaussian mixture model, etc.) to obtain a more accurate call for certain sequence regions by reducing noise and verifying a true copy or partial copy (e.g., due to a partial exon deletion).

At step 314, one or more of the systems described herein may perform a breakpoint analysis on a set of fragment sequences of the plurality of fragment sequences to i) identify at least one sequence variation located between selected breakpoint regions of the target gene, and ii) calculate modified copy number likelihoods for base positions of the reference sequence based on the at least one sequence variation, the modified copy number likelihoods each including a modification to a respective copy number likelihood indicating an increase or decrease in evidence for a copy number variation in the target gene at the corresponding base position of the reference sequence. For example, breakpoint module 228 in FIG. 2 may include a breakpoint caller that performs a breakpoint analysis on a set of fragment sequences of the plurality of fragment sequences. In at least one embodiment, the breakpoint analysis may be performed when the copy number likelihoods calculated based on read depths for base positions located between the selected breakpoint regions are below a specified threshold.

In at least one embodiment, breakpoint module 228 may identify at least one sequence variation located between selected breakpoint regions of the target gene. A "breakpoint" as used herein refers to a point in a sequencing read located between a region that matches a reference sequence and a region that differs from a reference sequence. In some embodiments, the breakpoint caller may, for example, identify a soft-clipping or an alternative mapping of an NGS sequencing read for a sample (e.g., as indicated by BWA alignment software). The start and/or stop point of the soft-clipping or alternative mapping may be identified as a breakpoint. As used herein, a "breakpoint region" refers to a sequence region that may include a breakpoint located between adjacent base pairs that results in a sequence variation. Breakpoint regions may be identified based on breakpoints observed in other genomic DNA samples (e.g., breakpoints identified in one or more sequence databases) or may be identified as regions that are likely to include breakpoints based on sequencing results and/or statistical modeling. Accordingly, a breakpoint region in the genomic DNA sample does not necessarily include a breakpoint, but a breakpoint may potentially or likely occur within the breakpoint region. In some embodiments, one or more breakpoint regions may be identified based on the alignment of the fragment sequences isolated from a sample with respect to the reference sequence, as determined in step 308 of the exemplary method disclosed herein.

Figure 4:
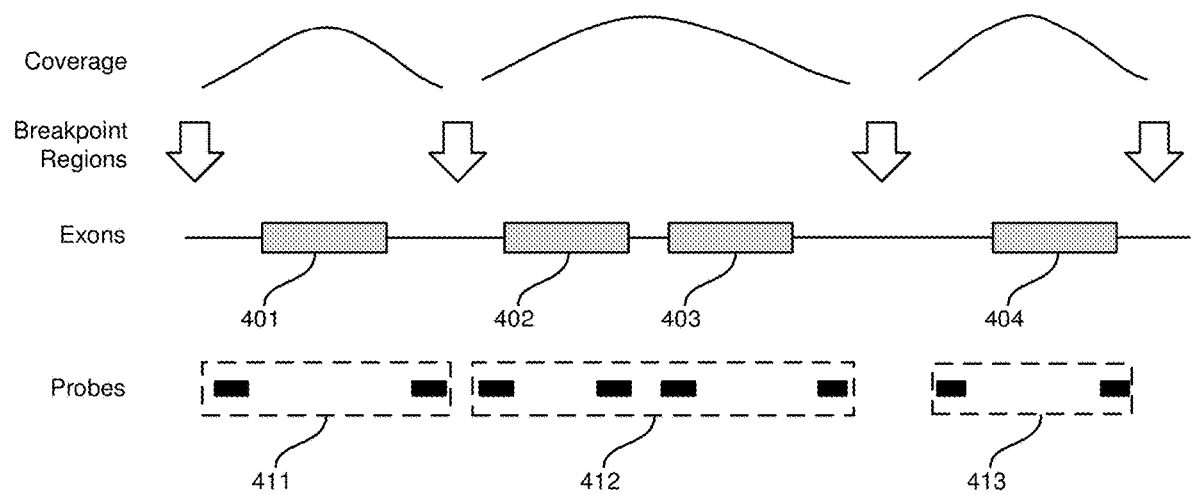
FIG. 4 is a diagram illustrating an exemplary portion of a reference sequence and exemplary probes and breakpoint.

FIG. 4 illustrates an exemplary portion of a reference sequence and corresponding read depth of coverage for samples aligned to the reference sequence according to the methods and systems described herein. As shown in FIG. 4, a portion of a reference sequence may include, for example, exons 401, 402, 403, and 404, with introns located between each of the respective exons. As shown, the read depth of coverage may be obtained corresponding to each of the exons. In one embodiment, breakpoint regions (shown by the arrows in FIG. 4) may be identified on introns located on either side of exon 401 and exon 404, between exon 401 and exon 402, and between exon 403 and exon 404.

Breakpoint module 228 may use a breakpoint caller to determine if at least one sequence variation is present between two or more of the breakpoint regions near exon 401, 402, 403, and/or 404. Sequencing data for sequences corresponding to a plurality of probes (i.e., breakpoint probes) located near the breakpoint regions may be modeled by the breakpoint caller to identify copy number likelihoods for selected sequence region 411, which includes exon 401, sequence region 412, which includes exons 402 and 403, and sequence region 413, which includes exon 404. A "breakpoint probe" as used herein refers to a probe designed to target a chromosome region where breakpoints in structural variation have been observed in one or more other samples such that a sequencing read obtained from polynucleotide fragments isolated using the probe may span at least a portion of a breakpoint region of a sample. Breakpoint regions targeted by breakpoint probes may be identified, for example, from sequenced samples having known structural variations in the corresponding breakpoint regions. The breakpoint probes may be selected probes of the plurality of probes (e.g., hybrid capture probes) used to isolate the plurality of target polynucleotide fragments. Fragment sequences corresponding to any suitable number breakpoint probes may be utilized in the breakpoint analysis, without limitation. In at least one embodiment, some or all of the breakpoint probes may be probes of the plurality of probes that hybridize to sequence regions including one or more of the breakpoint regions. For example, the breakpoint probes may be probes of the plurality of probes that hybridize to sequence regions located closest to the selected breakpoint regions with respect to the reference sequence. As shown in FIG. 4, for example, sequence region 411 may correspond to 2 breakpoint probes, sequence region 412 may correspond to 4 breakpoint probes, and sequence region 413 may correspond to 2 breakpoint probes.

Figure 5:
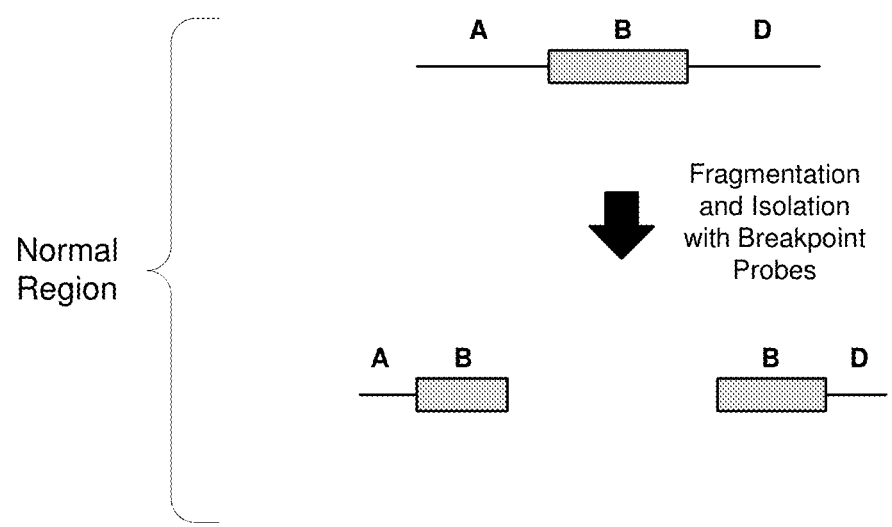
FIG. 5 is a diagram illustrating exemplary types of polynucleotide fragments that may be isolated from a normal region of a target gene and types of polynucleotide fragments that may be isolated from a copy number variant region of the target gene.
Figure 5:
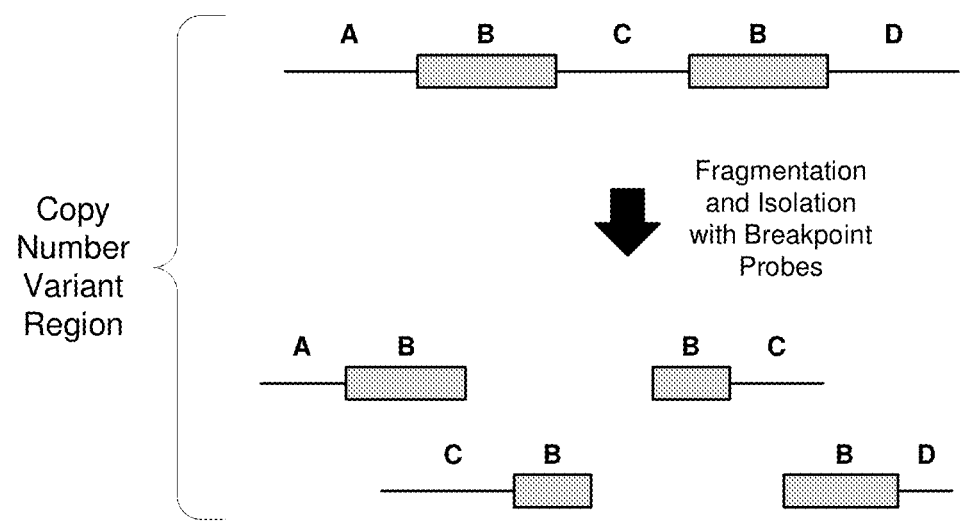

FIG. 5 illustrates exemplary types of polynucleotide fragments that may be isolated from a normal region (i.e., a region matching a corresponding portion of the target sequence) of the target gene and types of polynucleotide fragments that may be isolated from a copy number variant region. The normal region of the target gene includes sequence sections "A," "B," and "D." In contrast, the copy number variant region of the target region shown in FIG. 5 includes a duplication of sequence section "B," with an additional sequence section "C" between the two copies of "B." Following fragmentation of the genomic DNA including the normal region of the target gene, breakpoint probes may hybridize to and isolate fragments including at least a portion of "A-B" and fragments including at least a portion of "B-D." However, following fragmentation of the genomic DNA including a copy number variant region of the target gene, breakpoint probes may isolate fragments including at least a portion of "A-B," as well as additional fragments including at least a portion of "B-C," "C-B," and "B-D." Such fragments from the copy number variant region may not align properly with the portions of the reference sequence and may result in poor copy calls using conventional models. In such situations, the breakpoint caller may be utilized to further identify the copy number variants (or lack thereof) and provide a better copy call.

Figure 6:
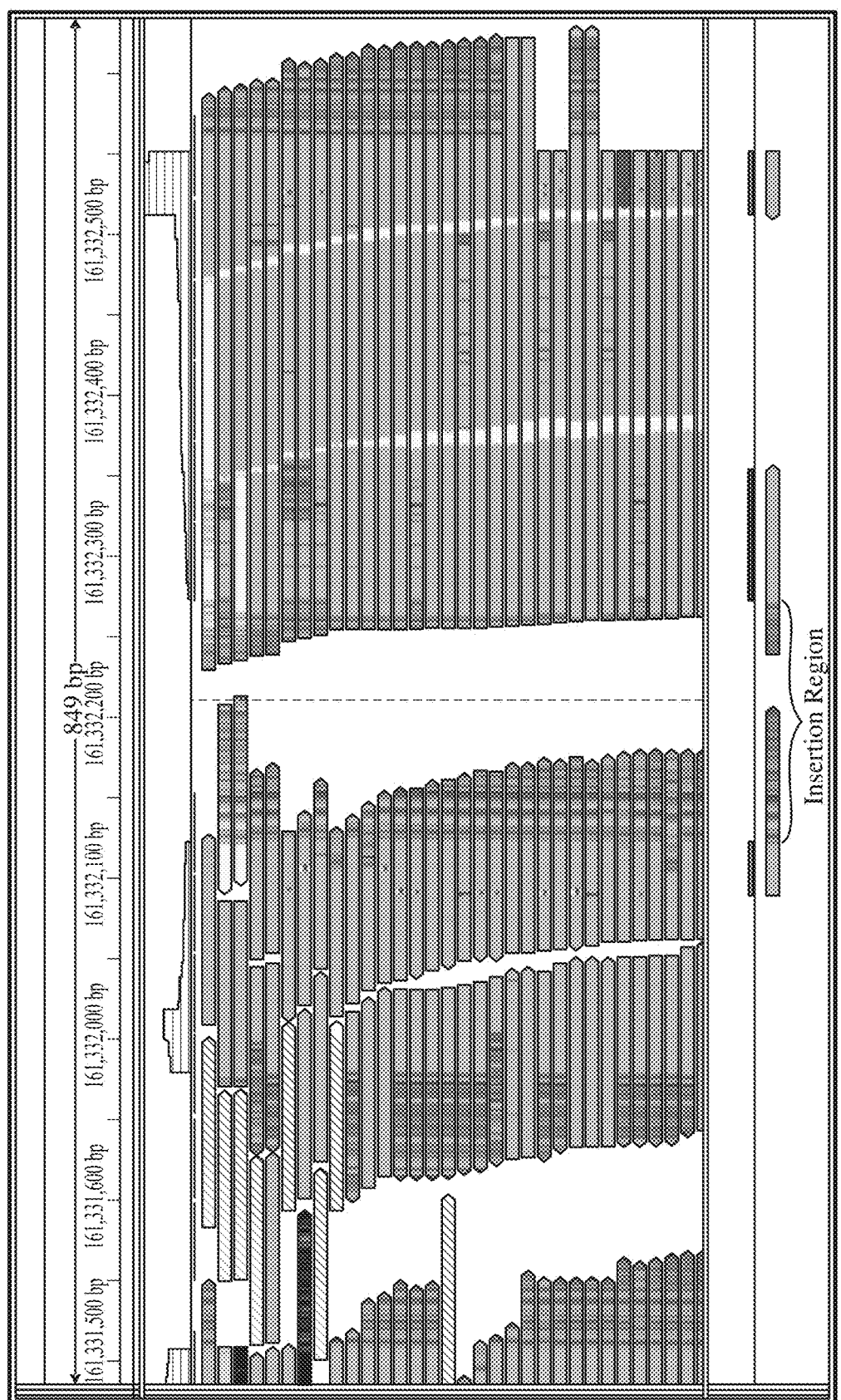
FIGS. 6-8 illustrate fragment sequences that are aligned to a reference sequence and that include various types of sequence variations with respect to the reference sequences.
Figure 7:
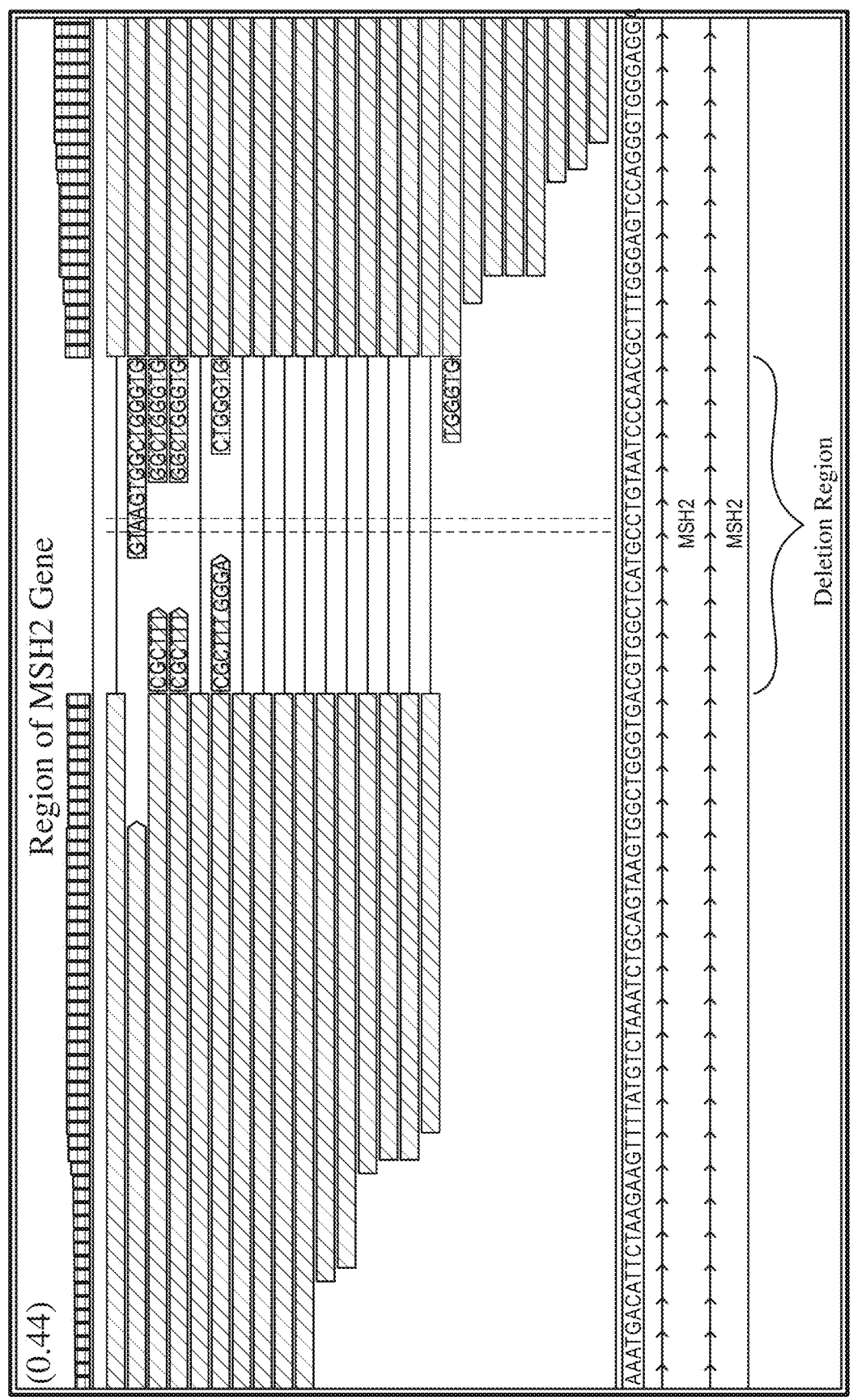
Figure 8:
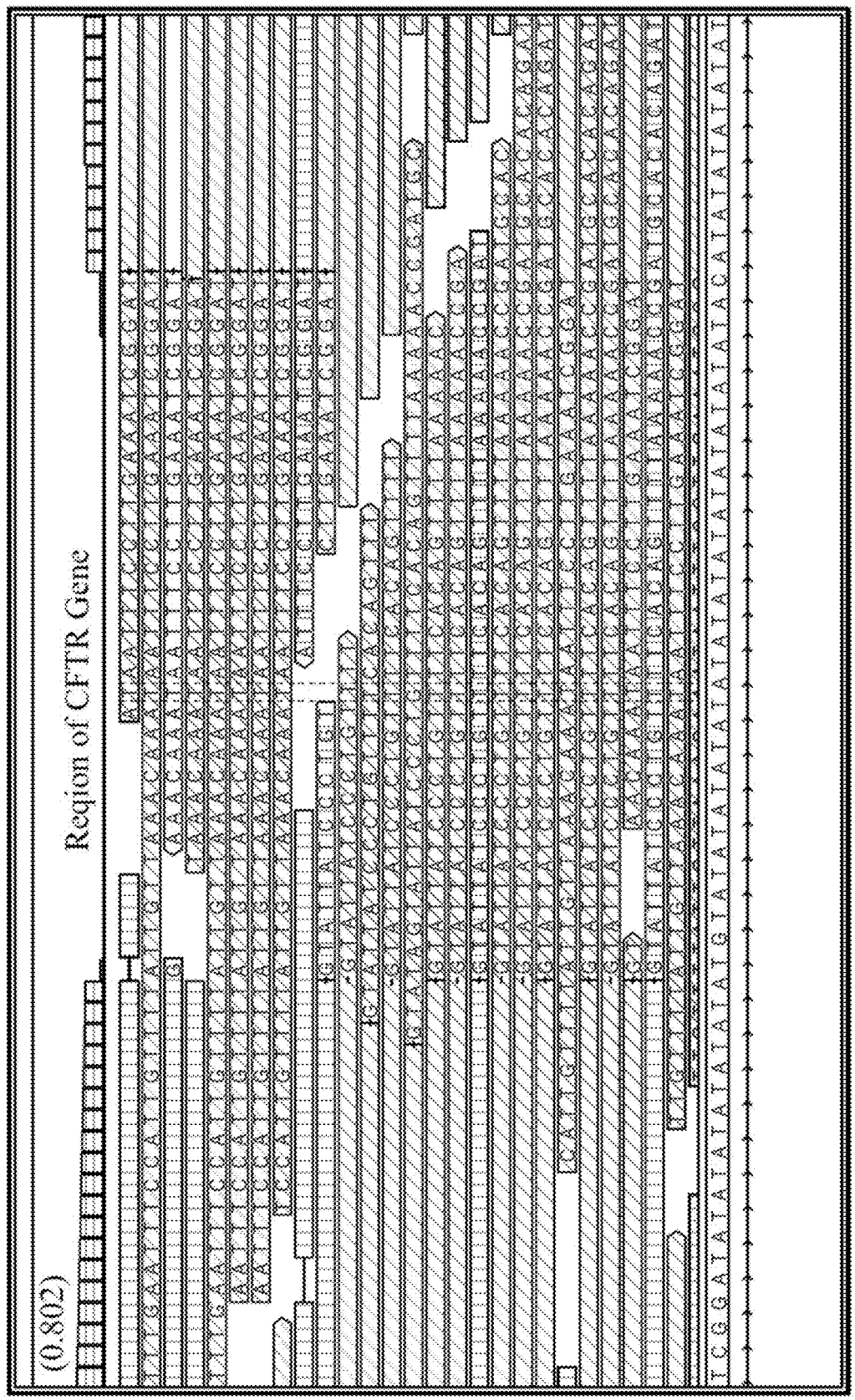

FIGS. 6-8 show various types of exemplary sequence variations that have been identified by the breakpoint caller described herein. For example, FIG. 6 shows isolated polynucleotide fragments that have been sequenced, pooled with BWA (Burrows-Wheeler Aligner, an open-source computer software program that aligns NGS reads to a reference genome), and aligned to a reference sequence. As shown in FIG. 6, the fragment sequences are mapped to a region determined to include a sequence insertion using the methods and systems described herein. FIG. 7 shows isolated polynucleotide fragments from a portion of the MSH2 gene that have been sequenced, pooled with BWA, and aligned to a reference MSH2 gene sequence comprising a polynucleotide sequence depicted in SEQ ID NO: 1. As shown in FIG. 7, the disclosed systems and methods determined that a sequence deletion is located at an intron portion of the MSH2 gene. FIG. 8 shows isolated polynucleotide fragments from a portion of the CFTR gene that have been sequenced, pooled with BWA, and aligned to a reference CFTR gene sequence comprising a polynucleotide sequence depicted in SEQ ID NO: 2. As shown in FIG. 8, the disclosed systems and methods determined that a $(TA)_n$ polymorphism is located in an intron of the CFTR gene.

The breakpoint caller of breakpoint module 228 may determine likelihoods that each of a plurality of types of sequence variation and/or copy number variation are present between the two or more of the selected breakpoint regions of the target gene. For example, the breakpoint caller may determine likelihoods that one or more of a plurality of types of copy number variation are present between breakpoint regions or whether no copy number variation exists between the breakpoint regions.

Returning to the exemplary sequence regions illustrated in FIG. 4, the breakpoint caller may calculate likelihoods that one or more of sequence regions 411, 412, and 413 are deleted in the target gene of the genomic DNA sample (relative to the corresponding reference sequence). Particularly, the breakpoint caller may calculate respective likelihoods that region 411 is deleted, that region 412 is deleted, that region 413 is deleted, that both of regions 411 and 412 are deleted, that both of regions 412 and 413 are deleted, and that all of regions 411, 412, and 413 are deleted in the target gene. The breakpoint caller may further calculate likelihoods that one or more of sequence regions 411, 412, and 413 are duplicated in the target gene of the genomic DNA sample (respective to the reference sequence). For example, the breakpoint caller may calculate respective likelihoods that region 411 is duplicated, that region 412 is duplicated, that region 413 is duplicated, that both of regions 411 and 412 are duplicated, that both of regions 412 and 413 are duplicated, and that all of regions 411, 412, and 413 are duplicated in the target gene of the genomic DNA sample. The breakpoint caller may additionally calculate a likelihood that none of regions 411, 412, and 413 are deleted or duplicated in the target gene of the genomic DNA sample.

An exemplary algorithm executed by the breakpoint caller of breakpoint module 228 may be structured according to the following pseudocode:

```
for sample in samples:
    for gene in genes:
        calculate_wt_log_likelihood( )
        for copy_number in [1, 3]:
            for probe_group_i in range(0, num_probe_groups):
                for probe_group_j in range(probe_group_i, num_probe_groups):
                    calculate_log_likelihood_of_copy_number_in_range_of_probe_group
                    s(copy_number, probe_group_i, probe_group_j)
        report_the_best_hypothesis( )
        integrate_with_breakpoint_results( )
```

The breakpoint caller may utilize any suitable statistical modeling to calculate modified copy number likelihoods for base positions of the reference sequence based on the at least one sequence variation. A copy number likelihood may be modified, for example, to indicate an increase or decrease in evidence for a particular copy number variation based on information obtained from a breakpoint analysis utilizing one or more breakpoint probes. For example, the calculated copy number likelihoods for each base position of the reference sequence based on the read depths may be modified based on the identification of one or more sequence variations. In some embodiments, at least some of the fragment sequences of the plurality of fragment sequences may be realigned to the reference sequence based on the one or more sequence variations prior to calculating the modified copy number likelihoods. In some embodiments, the reference sequence may be modified to better map and align the fragment sequences to the reference sequence. For example, the reference sequence may be modified to include one or more regions corresponding to duplicated, inserted, or deleted sequence regions identified by the breakpoint caller.

In at least one embodiment, calculating the modified copy number likelihoods for the base positions of the reference sequence may include calculating normalized read depths for the base positions of the plurality of target polynucleotide fragments relative to each base position of the reference sequence. The modified copy number likelihoods may be normalized, for example, based on sequencing and/or read depth data from one or more other genomic DNA samples.

Returning to FIG. 3, at step 316, one or more of the systems described herein may determine, based on the modified copy number likelihoods for the base positions of the reference sequence, whether the target gene includes at least one copy number variation. For example, copy number module 230 in FIG. 2 may determine, based on the modified copy number likelihoods for the base positions of the reference sequence, whether the target gene includes at least one copy number variation. In some embodiments, the modified copy number likelihoods may be combined with results from an initial copy caller (e.g., HMM, Gaussian mixture model, etc.) to better call the copy number at each region of the target gene. In some embodiments, determining whether the target gene includes at least one copy number variation may include determining, above a threshold probability, that at least one sequence variation is present between two or selected breakpoint regions of the target gene based on the respective likelihoods calculated for the plurality of types of sequence variation. The modified copy number likelihoods for the base positions of the reference sequence may be used to identify copy number variations with greater accuracy and higher probability while reducing noise present in the unmodified copy number likelihoods. In some embodiments, the modified copy number likelihoods for the base positions of the reference sequence may be used to confirm and/or to adjust copy numbers determined by an initial copy caller.

In at least one embodiment, the modified copy number likelihoods may include additional copy number likelihoods for bases corresponding to modified regions of the reference sequence. For example, the reference sequence may be modified to include one or more regions corresponding to duplicated, inserted, rearranged (e.g., inverted), or deleted sequence regions identified by the breakpoint caller, and corresponding modified copy number likelihoods may be added to correspond to these duplicated, inserted, rearrange, or deleted sequence regions.

Figure 9:
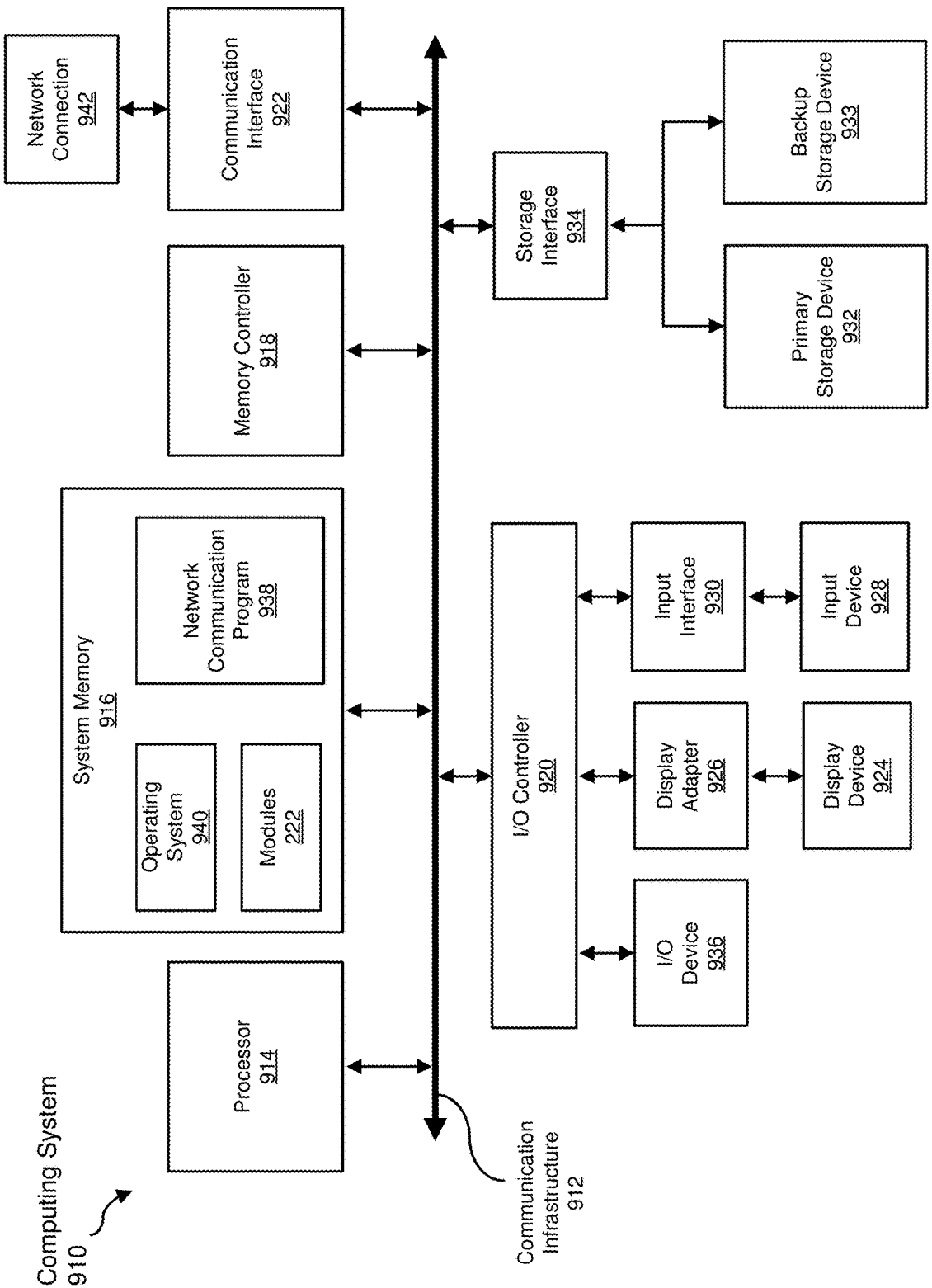
FIG. 9 is a block diagram of an example computing network capable of implementing one or more of the embodiments described and/or illustrated herein.

FIG. 9 is a block diagram of an example computing system 910 capable of implementing at least a portion of one or more of the embodiments described and/or illustrated herein. For example, all or a portion of computing system 910 may perform and/or be a means for performing, either alone or in combination with other elements, one or more of the steps described herein (such as one or more of the steps illustrated in FIG. 3). All or a portion of computing system 910 may also perform and/or be a means for performing any other steps, methods, or processes described and/or illustrated herein.

Computing system 910 broadly represents any single or multi-processor computing device or system capable of executing computer-readable instructions. Examples of computing system 910 include, without limitation, workstations, laptops, client-side terminals, servers, distributed computing systems, handheld devices, or any other computing system or device. In its most basic configuration, computing system 910 may include at least one processor 914 and a system memory 916.

Processor 914 generally represents any type or form of physical processing unit (e.g., a hardware-implemented central processing unit) capable of processing data or interpreting and executing instructions. In certain embodiments, processor 914 may receive instructions from a software application or module. These instructions may cause processor 914 to perform the functions of one or more of the example embodiments described and/or illustrated herein.

System memory 916 generally represents any type or form of volatile or non-volatile storage device or medium capable of storing data and/or other computer-readable instructions. Examples of system memory 916 include, without limitation, Random Access Memory (RAM), Read Only Memory (ROM), flash memory, or any other suitable memory device. Although not required, in certain embodiments computing system 910 may include both a volatile memory unit (such as, for example, system memory 916) and a non-volatile storage device (such as, for example, primary storage device 932, as described in detail below). In one example, one or more of modules 222 from FIG. 2 may be loaded into system memory 916.

In some examples, system memory 916 may store and/or load an operating system 940 for execution by processor 914. In one example, operating system 940 may include and/or represent software that manages computer hardware and software resources and/or provides common services to computer programs and/or applications on computing system 910. Examples of operating system 940 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 910 may also include one or more components or elements in addition to processor 914 and system memory 916. For example, as illustrated in FIG. 9, computing system 910 may include a memory controller 918, an Input/Output (I/O) controller 920, and a communication interface 922, each of which may be interconnected via a communication infrastructure 912. Communication infrastructure 912 generally represents any type or form of infrastructure capable of facilitating communication between one or more components of a computing device. Examples of communication infrastructure 912 include, without limitation, a communication bus (such as an Industry Standard Architecture (ISA), Peripheral Component Interconnect (PCI), PCI Express (PCIe), or similar bus) and a network.

Memory controller 918 generally represents any type or form of device capable of handling memory or data or controlling communication between one or more components of computing system 910. For example, in certain embodiments memory controller 918 may control communication between processor 914, system memory 916, and I/O controller 920 via communication infrastructure 912.

I/O controller 920 generally represents any type or form of module capable of coordinating and/or controlling the input and output functions of a computing device. For example, in certain embodiments I/O controller 920 may control or facilitate transfer of data between one or more elements of computing system 910, such as processor 914, system memory 916, communication interface 922, display adapter 926, input interface 930, and storage interface 934.

As illustrated in FIG. 9, computing system 910 may also include at least one display device 924 coupled to I/O controller 920 via a display adapter 926. Display device 924 generally represents any type or form of device capable of visually displaying information forwarded by display adapter 926. Similarly, display adapter 926 generally represents any type or form of device configured to forward graphics, text, and other data from communication infrastructure 912 (or from a frame buffer, as known in the art) for display on display device 924.

As illustrated in FIG. 9, example computing system 910 may also include at least one input device 928 coupled to I/O controller 920 via an input interface 930. Input device 928 generally represents any type or form of input device capable of providing input, either computer or human generated, to example computing system 910. Examples of input device 928 include, without limitation, a keyboard, a pointing device, a speech recognition device, variations or combinations of one or more of the same, and/or any other input device.

Additionally or alternatively, example computing system 910 may include additional I/O devices. For example, example computing system 910 may include I/O device 936. In this example, I/O device 936 may include and/or represent a user interface that facilitates human interaction with computing system 910. Examples of I/O device 936 include, without limitation, a computer mouse, a keyboard, a monitor, a printer, a modem, a camera, a scanner, a microphone, a touchscreen device, variations or combinations of one or more of the same, and/or any other I/O device.

Communication interface 922 broadly represents any type or form of communication device or adapter capable of facilitating communication between example computing system 910 and one or more additional devices. For example, in certain embodiments communication interface 922 may facilitate communication between computing system 910 and a private or public network including additional computing systems. Examples of communication interface 922 include, without limitation, a wired network interface (such as a network interface card), a wireless network interface (such as a wireless network interface card), a modem, and any other suitable interface. In at least one embodiment, communication interface 922 may provide a direct connection to a remote server via a direct link to a network, such as the Internet. Communication interface 922 may also indirectly provide such a connection through, for example, a local area network (such as an Ethernet network), a personal area network, a telephone or cable network, a cellular telephone connection, a satellite data connection, or any other suitable connection.

In certain embodiments, communication interface 922 may also represent a host adapter configured to facilitate communication between computing system 910 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 922 may also allow computing system 910 to engage in distributed or remote computing. For example, communication interface 922 may receive instructions from a remote device or send instructions to a remote device for execution.

In some examples, system memory 916 may store and/or load a network communication program 938 for execution by processor 914. In one example, network communication program 938 may include and/or represent software that enables computing system 910 to establish a network connection 942 with another computing system (not illustrated in FIG. 9) and/or communicate with the other computing system by way of communication interface 922. In this example, network communication program 938 may direct the flow of outgoing traffic that is sent to the other computing system via network connection 942. Additionally or alternatively, network communication program 938 may direct the processing of incoming traffic that is received from the other computing system via network connection 942 in connection with processor 914.

Although not illustrated in this way in FIG. 9, network communication program 938 may alternatively be stored and/or loaded in communication interface 922. For example, network communication program 938 may include and/or represent at least a portion of software and/or firmware that is executed by a processor and/or Application Specific Integrated Circuit (ASIC) incorporated in communication interface 922.

As illustrated in FIG. 9, example computing system 910 may also include a primary storage device 932 and a backup storage device 933 coupled to communication infrastructure 912 via a storage interface 934. Storage devices 932 and 933 generally represent any type or form of storage device or medium capable of storing data and/or other computer-readable instructions. For example, storage devices 932 and 933 may be a magnetic disk drive (e.g., a so-called hard drive), a solid state drive, a floppy disk drive, a magnetic tape drive, an optical disk drive, a flash drive, or the like. Storage interface 934 generally represents any type or form of interface or device for transferring data between storage devices 932 and 933 and other components of computing system 910.

In certain embodiments, storage devices 932 and 933 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 932 and 933 may also include other similar structures or devices for allowing computer software, data, or other computer-readable instructions to be loaded into computing system 910. For example, storage devices 932 and 933 may be configured to read and write software, data, or other computer-readable information. Storage devices 932 and 933 may also be a part of computing system 910 or may be a separate device accessed through other interface systems.

Many other devices or subsystems may be connected to computing system 910. Conversely, all of the components and devices illustrated in FIG. 9 need not be present to practice the embodiments described and/or illustrated herein. The devices and subsystems referenced above may also be interconnected in different ways from that shown in FIG. 9. Computing system 910 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 910. All or a portion of the computer program stored on the computer-readable medium may then be stored in system memory 916 and/or various portions of storage devices 932 and 933. When executed by processor 914, a computer program loaded into computing system 910 may cause processor 914 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 910 may be configured as an Application Specific Integrated Circuit (ASIC) adapted to implement one or more of the example embodiments disclosed herein.

In addition, one or more of the modules described herein may transform data, physical devices, and/or representations of physical devices from one form to another. For example, one or more of the modules recited herein may receive sequence data to be transformed, transform the sequence data to copy number data for regions of a target gene, output a result of the transformation to a user terminal, use the result of the transformation to more accurately determine and quantify copy number variations, and store the result of the transformation to storage device and/or database. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

EXAMPLES

The present invention is described in further detail in the following examples which are not in any way intended to limit the scope of the invention as claimed. The attached figures are meant to be considered as integral parts of the specification and description of the invention. All references cited are herein specifically incorporated by reference for all that is described therein. The following examples are offered to illustrate, but not to limit the claimed invention.

Example 1

Identifying and Quantifying Gene Copy Number Variation

This example illustrates the method for identifying and quantifying gene copy number variation.

Figure 10:
FIGS. 10-13 are example charts showing copy number variation determinations using the systems and methods disclosed herein.
Figure 11:
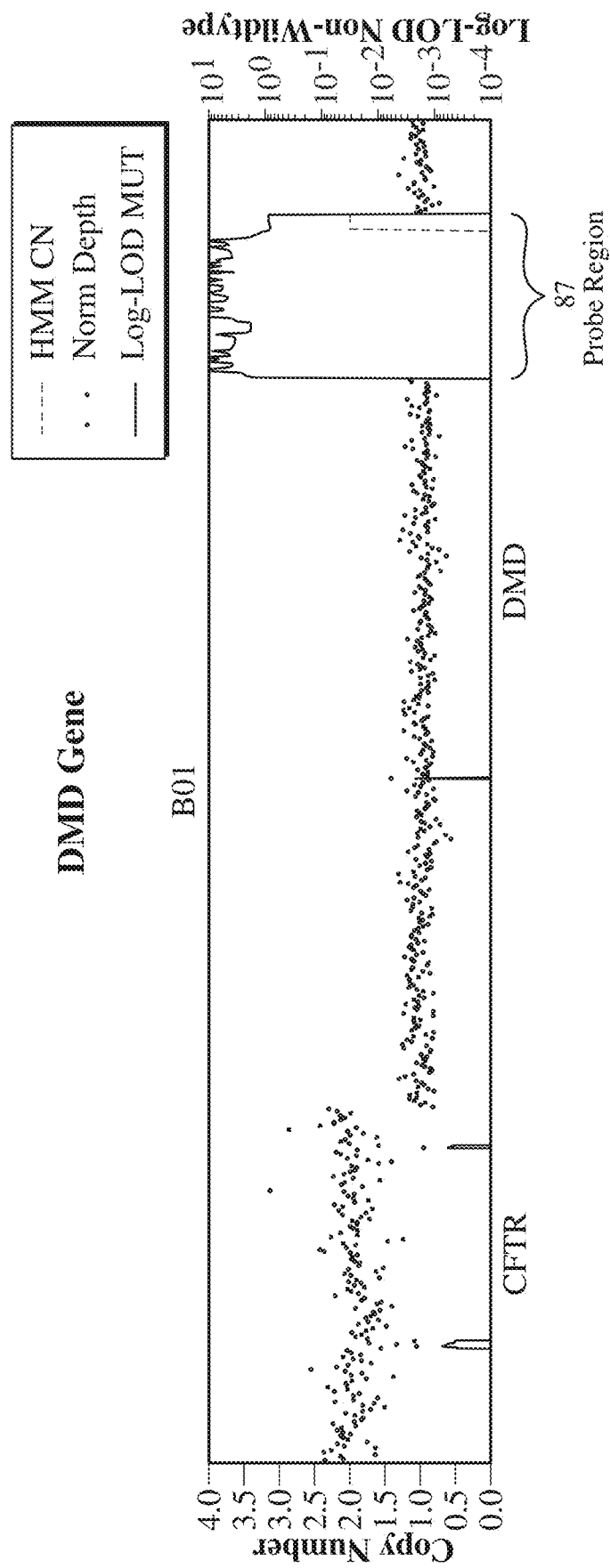

The method includes the following steps.
1. Fragmented individual genomic DNA sample and isolated a plurality of target polynucleotide fragments using capture probes, including probes suitable for breakpoint analysis of specified regions.
2. Sequenced the target polynucleotide fragments and aligned the fragment sequences to a reference sequence using BWA.
3. Calculated read depth (i.e., the number of aligned reads) for base positions of the DMD gene based on the sequence of the read (optionally adjust read depth to take GC bias into account).
4. Calculated copy number likelihoods for each base position of the reference DMD gene sequence based on the calculated read depths.
5. Performed breakpoint analysis on a set of fragment sequences aligned to the DMD gene sequence to identify at least one sequence variation located between selected breakpoint regions of the target gene. As shown in FIGS. 10 and 11, a portion of the DMD gene sequence corresponding to 87 capture probes (i.e., breakpoint probes) was determined to include a sequence variation by the breakpoint caller.
6. Calculated, by the breakpoint caller, modified copy number likelihoods for base positions of the reference DMD gene sequence based on the sequence variation.
7. Determined, based on the modified copy number likelihoods for the base positions of the reference sequence, whether the target gene includes at least one copy number variation. The DMD gene sample was determined to have a copy number variation in the 87 probe region based on the breakpoint analysis.

As shown in FIGS. 10 and 11, portions of the DMD gene outside the 87 probe region were not subjected to the further breakpoint analysis since copy number likelihoods for these regions were high following the read depth calculation and deemed to accurately correspond a copy number of 1. However, the 87 probe region was selected for further breakpoint analysis to identify sequence variations and any corresponding copy number variations. A copy number of 0 was determined, with a high probability, in the 87 probe region following the breakpoint analysis.

Example 2

This example illustrates the method for identifying and quantifying gene copy number variation.

Figure 12:
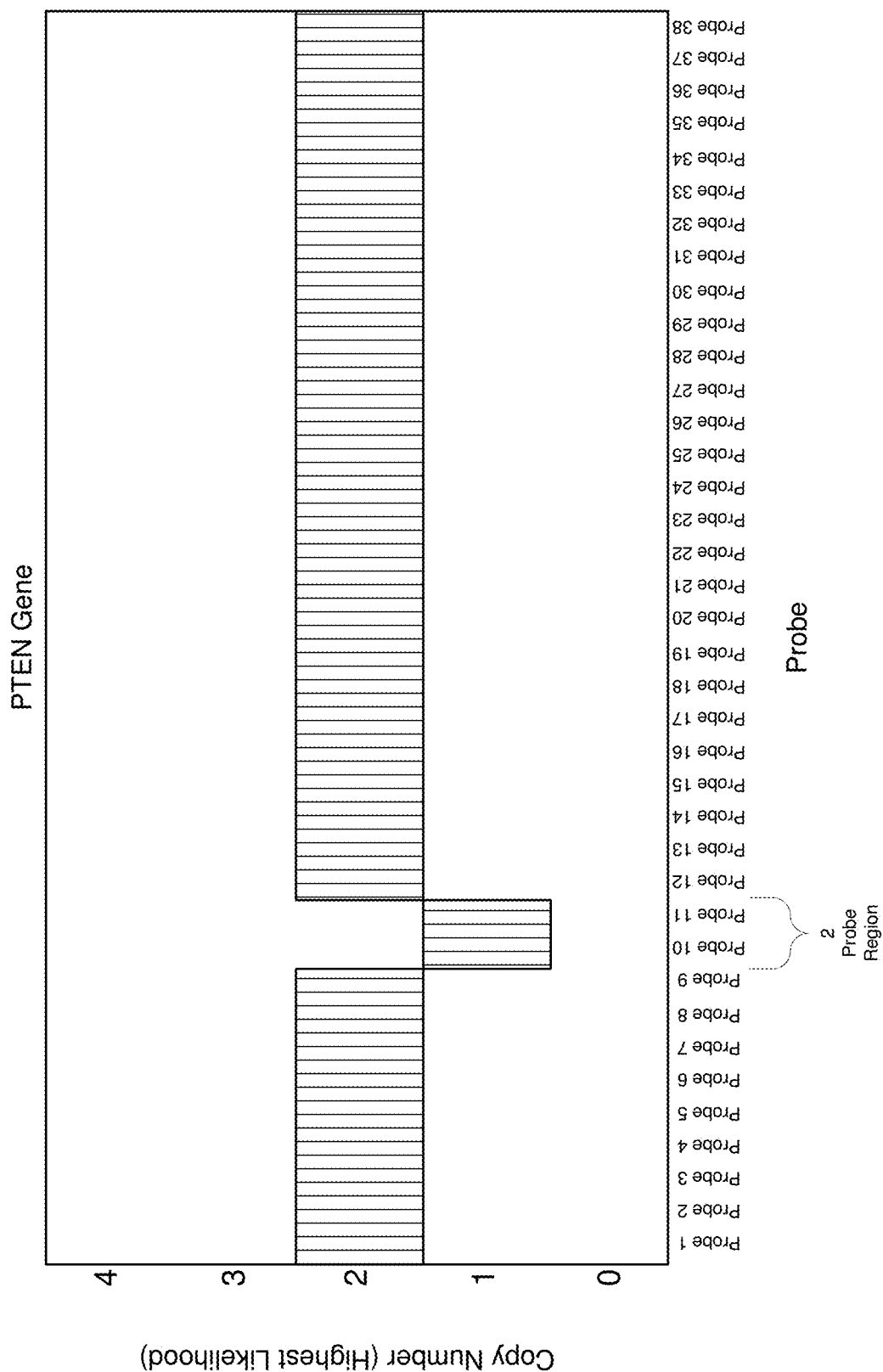

The method includes the following steps.
1. Fragmented individual genomic DNA sample and isolated a plurality of target polynucleotide fragments using capture probes, including probes suitable for breakpoint analysis of specified regions.
2. Sequenced the target polynucleotide fragments and aligned the fragment sequences to a reference sequence using BWA.
3. Calculated read depth for base positions of the PTEN gene based on the sequence of the read.
4. Calculated copy number likelihoods for each base position of the reference PTEN gene sequence based on the calculated read depths.
5. Performed breakpoint analysis on a set of fragment sequences aligned to the PTEN gene sequence to identify at least one sequence variation located between selected breakpoint regions of the target gene. As shown in FIG. 12, a portion of the PTEN gene sequence corresponding to 2 capture probes was determined to include a sequence variation by the breakpoint caller.
6. Calculated, by the breakpoint caller, modified copy number likelihoods for base positions of the reference PTEN gene sequence based on the sequence variation.
7. Determined, based on the modified copy number likelihoods for the base positions of the reference sequence, whether the target gene includes at least one copy number variation. The PTEN gene sample was determined to have a copy number variation in the 2 probe region based on the breakpoint analysis.

As shown in FIG. 12, the 2 probe sequence region (i.e., region including probes 10 and 11) was selected for further breakpoint analysis to identify sequence variations and any corresponding copy number variations. The copy number was determined, with a high probability, to be 1 in the region of probes 10 and 11 following the breakpoint analysis.

Example 3

This example illustrates the method for identifying and quantifying gene copy number variation.

Figure 13:
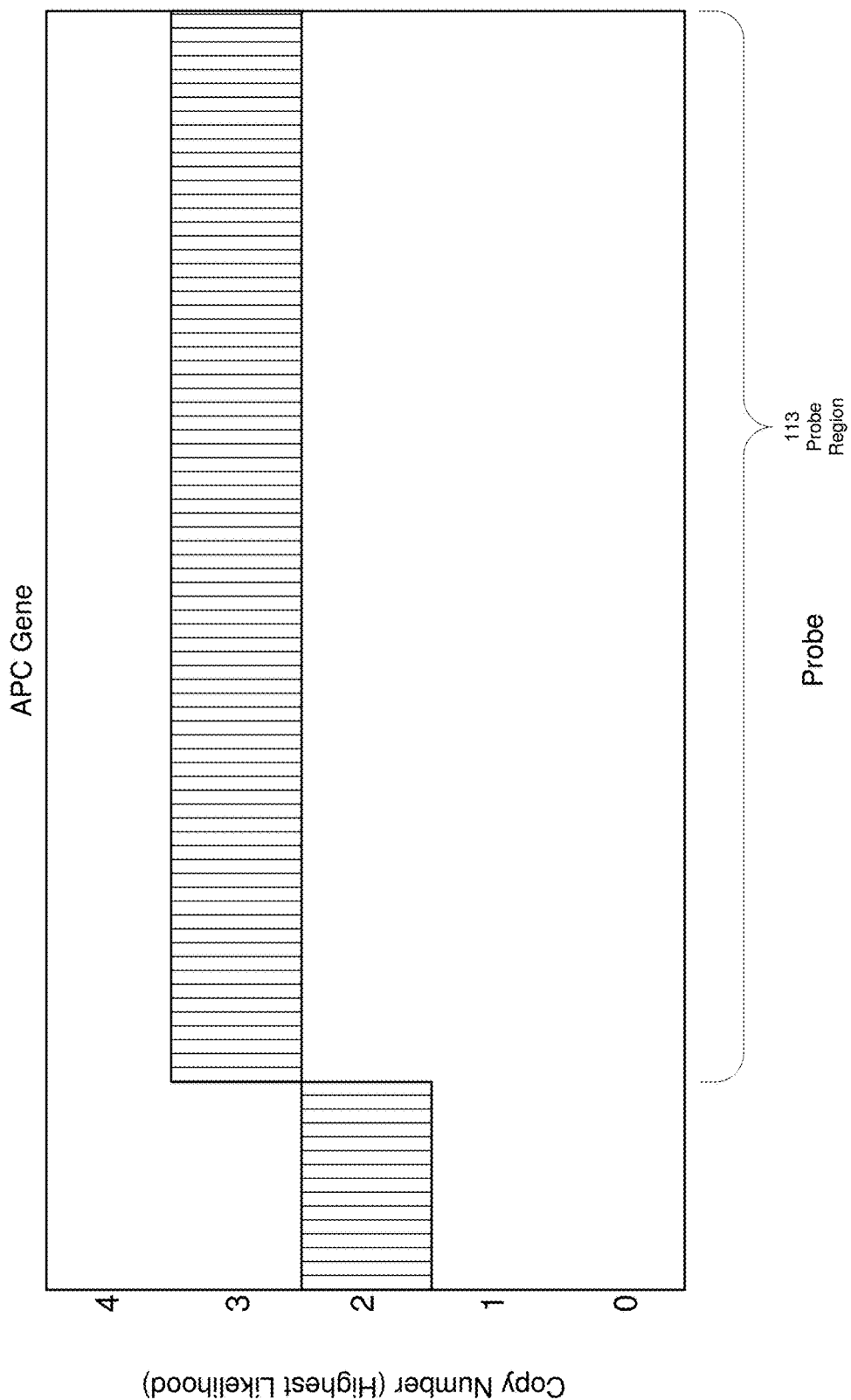

The method includes the following steps.
1. Fragmented individual genomic DNA sample and isolated a plurality of target polynucleotide fragments using capture probes, including probes suitable for breakpoint analysis of specified regions.
2. Sequenced the target polynucleotide fragments and aligned the fragment sequences to a reference sequence using BWA.
3. Calculated read depth for base positions of the APC gene based on the sequence of the read.
4. Calculated copy number likelihoods for each base position of the reference APC gene sequence based on the calculated read depths.
5. Performed breakpoint analysis on a set of fragment sequences aligned to the APC gene sequence to identify at least one sequence variation located between selected breakpoint regions of the target gene. As shown in FIG. 13, a portion of the APC gene sequence corresponding to 113 capture probes was determined to include a sequence variation by the breakpoint caller.
6. Calculated, by the breakpoint caller, modified copy number likelihoods for base positions of the reference APC gene sequence based on the sequence variation.
7. Determined, based on the modified copy number likelihoods for the base positions of the reference sequence, whether the target gene includes at least one copy number variation. The APC gene sample was determined to have a copy number variation in the 113 probe region based on the breakpoint analysis.

As shown in FIG. 13, the 113 probe sequence region was selected for further breakpoint analysis to identify sequence variations and any corresponding copy number variations. The copy number was determined, with a high probability, to be 3 in the 113 probe region following the breakpoint analysis.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

While various aspects and embodiments have been disclosed herein, other aspects and embodiments are contemplated. The various aspects and embodiments disclosed herein are for purposes of illustration and are not intended to be limiting. Unless otherwise noted, the terms "a" or "an," as used in the specification and claims, are to be construed as meaning "at least one of." In addition, for ease of use, the words "including" and "having," and variants thereof (e.g., "includes" and "has") as used in the specification and claims, are interchangeable with and have the same meaning as the word "comprising" and variants thereof (e.g., "comprise" and "comprises").

---

---

What is claimed is:

1. A method of identifying and quantifying copy number variations in a gene of interest from a genomic deoxyribonucleic acid (DNA) sample, the method comprising;
   fragmenting a genomic DNA sample having an unknown copy number for regions of a target gene to produce a plurality of polynucleotide fragments;
   isolating a plurality of target polynucleotide fragments from the plurality of polynucleotide fragments by using a plurality of breakpoint probes to isolate target polynucleotide fragments comprising one or more breakpoint regions, each of the plurality of target polynucleotide fragments including at least a portion of the target gene, wherein the plurality of breakpoint probes target a chromosome region where one or more breakpoints in structural variation are selected from the group consisting of: duplication, deletion, insertion, translocation, interchange, fusion, and inversion that have been observed in one or more other samples;

sequencing the plurality of target polynucleotide fragments to obtain a plurality of fragment sequences; and via a computing device: aligning fragment sequences of the plurality of fragment sequences to a reference sequence;

calculating read depths for base positions of the plurality of target polynucleotide fragments relative to each base position of the reference sequence;

calculating copy number likelihoods for each base position of the reference sequence based on the read depths to make a call on at least one copy number variation in the target gene;

performing a breakpoint analysis on a set of fragment sequences of the plurality of fragment sequences to:
identify at least one sequence variation located between selected breakpoint regions of the target gene, wherein the selected breakpoint regions comprise sequence regions that include a breakpoint between adjacent base pairs that result in the at least one sequence variation, and wherein the breakpoint comprises a point in a sequencing read located between a region of the target gene that matches the reference sequence and a region of the target gene that differs from the reference sequence; and calculate modified copy number likelihoods for base positions of the reference sequence based on the at least one sequence variation, the modified copy number likelihoods each including a modification to a respective copy number likelihood indicating an increase or decrease in evidence for a copy number variation in the target gene at the corresponding base position of the reference sequence; and correcting, based on the modified copy number likelihoods for the base positions of the reference sequence, the call on the at least one copy number variation in the target gene when the modified copy number likelihoods breach a threshold probability.

2. The method of claim 1, further comprising:
partitioning each of the plurality of fragment sequences to either the target gene or a homolog of the target gene;
wherein aligning the fragment sequences of the plurality of fragment sequences to the reference sequence comprises aligning fragment sequences partitioned to the target gene to the reference sequence, which is a target gene reference sequence.

3. The method of claim 2, further comprising aligning additional fragment sequences partitioned to the homolog of the target gene to a homolog gene reference sequence.

4. The method of claim 1, wherein the set of fragment sequences on which the breakpoint analysis is performed comprises fragment sequences that are at least partially located between the selected breakpoint regions of the target gene.

5. The method of claim 1, wherein the set of fragment sequences on which the breakpoint analysis is performed comprises fragment sequences that include the selected breakpoint regions of the target gene.

6. The method of claim 5, wherein the fragment sequences that include the selected breakpoint regions of the target gene include a sequence variation on one side of at least one of the selected breakpoint regions.

7. The method of claim 1, wherein the plurality of breakpoint probes comprise capture probes that hybridize to a selected breakpoint region observed in at least one other sample.

8. The method of claim 7, wherein the plurality of capture probes are hybrid capture probes.

9. The method of claim 7, wherein the set of fragment sequences on which the breakpoint analysis is performed comprises fragment sequences having portions that hybridize to the breakpoint probes.

10. The method of claim 9, wherein the breakpoint probes hybridize to sequence regions located closest to the selected breakpoint regions with respect to the reference sequence.

11. The method of claim 9, wherein the breakpoint probes hybridize to sequence regions located between the selected breakpoint regions with respect to the reference sequence.

12. The method of claim 1, wherein performing the breakpoint analysis on the set of fragment sequences of the plurality of fragment sequences further comprises determining a likelihood that each of a plurality of types of sequence variation are present between the selected breakpoint regions of the target gene.

13. The method of claim 12, wherein the plurality of types of sequence variation respectively correspond to a plurality of types of copy number variation and no copy number variation.

14. The method of claim 13, wherein the plurality of types of copy number variation respectively correspond to at least one deletion and at least one duplication of one or more of the regions of the target gene.

15. The method of claim 12, wherein determining whether the target gene includes at least one copy number variation comprises determining, above a threshold probability, that the at least one sequence variation is present between the selected breakpoint regions of the target gene based on the respective likelihoods calculated for the plurality of types of sequence variation.

16. The method of claim 12, wherein the plurality of types of sequence variation include a deletion, an insertion, an inversion, a translocation, an interchange, and a fusion.

17. The method of claim 1, wherein the breakpoint analysis is performed when the copy number likelihoods calculated based on read depths for base positions located between the selected breakpoint regions are below a specified threshold.

18. The method of claim 1, wherein the reference sequence comprises a sequence from a reference genome.

19. The method of claim 1, wherein calculating the modified copy number likelihoods for the base positions of the reference sequence comprises calculating normalized read depths for the base positions of the plurality of target polynucleotide fragments relative to each base position of the reference sequence.

20. A system for identifying and quantifying copy number variations in a gene of interest from a genomic DNA sample, the system comprising:
(1) a next generation sequencing device that:
(i) fragments a genomic DNA sample having an unknown copy number for regions of a target gene to produce a plurality of polynucleotide fragments;
(ii) isolates a plurality of target polynucleotide from the plurality of polynucleotide fragments by using a plurality of breakpoint probes to isolate target polynucleotide fragments comprising one or more breakpoint regions, each of the plurality of target polynucleotide fragments including at least a portion of the target gene, wherein the plurality of breakpoint probes target a chromosome region where one or more breakpoints in structural variation are selected from the group consisting of: duplication, deletion, insertion, translocation, interchange, fusion, and inversion that have been observed in one or more other samples; and (iii) sequences the plurality of target polynucleotide fragments to obtain a plurality of fragment sequences;

(2) an alignment module, stored in memory, that aligns fragment sequences of the plurality of fragment sequences to a reference sequence;

(3) a read depth module, stored in memory, that:
  (i) calculates read depths for base positions of the plurality of target polynucleotide fragments relative to each base position of the reference sequence; and
  (ii) calculates copy number likelihoods for each base position of the reference sequence based on the read depths to make a call on at least one copy number variation in the target gene;

(4) a breakpoint module, stored in memory, that performs a breakpoint analysis on a set of fragment sequences of the plurality of fragment sequences to:
  (i) identify at least one sequence variation located between selected breakpoint regions of the target gene, wherein the selected breakpoint regions comprise sequence regions that include a breakpoint between adjacent base pairs that result in the at least one sequence variation, and wherein the breakpoint comprises a point in a sequencing read located between a region of the target gene that matches the reference sequence and a region of the target gene that differs from the reference sequence; and
  (ii) calculate modified copy number likelihoods for base positions of the reference sequence based on the at least one sequence variation, the modified copy number likelihoods each including a modification to a respective copy number likelihood indicating an increase or decrease in evidence for a copy number variation in the target gene at the corresponding base position of the reference sequence;

(5) a copy number module, stored in memory, that corrects, based on the modified copy number likelihoods for the base positions of the reference sequence, the call on the at least one copy number variation in the target gene when the modified copy number likelihoods breach a threshold probability; and (6) at least one physical processor that executes the alignment module, the read depth module, the breakpoint module, and the copy number module.

* * * * *

SEQUENCE LISTING

<160> NUMBER OF SEQ ID NOS: 2

<210> SEQ ID NO 1
<211> LENGTH: 103
<212> TYPE: DNA
<213> ORGANISM: Homo sapiens

<400> SEQUENCE: 1
aaatgacatt ctaagaagtt ttatgtctaa atctgcagta agtggctggg tgacgtggct    60
catgcctgta atcccaacgc tttgggagtc cagggtggga gga                     103

<210> SEQ ID NO 2
<211> LENGTH: 64
<212> TYPE: DNA
<213> ORGANISM: Homo sapiens

<400> SEQUENCE: 2
tcggatatat atatatatat gtatatatat atatatatat atatatatat acatatatat    60
atat                                                                64